(12) United States Patent
O'Brien et al.

(10) Patent No.: US 12,708,318 B2
(45) **Date of Patent: *Aug. 18, 2026**

(54) SYSTEMS, METHODS, AND DEVICES FOR DETECTING THE THRESHOLD OF NERVE-MUSCLE RESPONSE USING VARIABLE FREQUENCY OF STIMULATION

(71) Applicant: Alphatec Spine, Inc., Carlsbad, CA (US)

(72) Inventors: Richard A. O'Brien, Cockeysville, MD (US); Gregg Johns, Oceanside, CA (US); Robert Snow, Phoenix, MD (US); James E. Gharib, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 523 days.

This patent is subject to a terminal disclaimer.

(21) Appl. No.: 18/352,975

(22) Filed: Jul. 14, 2023

(65) Prior Publication Data

US 2023/0371876 A1 Nov. 23, 2023

Related U.S. Application Data

(63) Continuation of application No. 16/010,157, filed on Jun. 15, 2018, now Pat. No. 11,701,047.

(Continued)

(51) Int. Cl.

*A61B 5/395* (2021.01)
*A61B 5/00* (2006.01)

(Continued)

(52) U.S. Cl.

CPC .............. *A61B 5/395* (2021.01); *A61B 5/388* (2021.01); *A61B 5/7214* (2013.01);

(Continued)

(58) Field of Classification Search

CPC ............ A61B 5/04012; A61B 5/04001; A61B 5/0488; A61B 5/7214; A61B 5/7264; A61B 5/746; A61N 1/36017; G16H 20/30

See application file for complete search history.

(56) References Cited

U.S. PATENT DOCUMENTS 4,161,945 A 7/1979 Grossman
4,291,703 A 9/1981 Kelen (Continued)

FOREIGN PATENT DOCUMENTS

CN 1744929 A 3/2006
CN 101137332 A 3/2008

(Continued)

OTHER PUBLICATIONS

"NeuroStream—Intraoperative Monitoring Document Management" [online][retrieved Apr. 21, 2010). Retrieved from the Internet at <http://www.neurostream.us/solutionsonlineDoc.iso?nav=1>.

(Continued)

*Primary Examiner* — Patrick Fernandes
(74) *Attorney, Agent, or Firm* — Dentons Durham Jones Pinegar; Sarah W. Matthews

(57) ABSTRACT

A method for determining a lowest stimulation threshold current level in a group of channels of a neuromonitoring device. The method includes stimulating tissue at a current level from a predetermined range of current levels as a sequence of pulses delivered at a frequency. The stimulating includes increasing the current level of each pulse in the sequence of pulses from an immediately preceding pulse by a first current increment. The method includes determining that a first evocation pulse from the sequence of pulses evokes a first muscular response. The method includes stimulating the tissue with a second evocation pulse from the sequence of pulses to evoke a second muscular response. The stimulating includes decreasing the frequency of the (Continued)

delivery of each pulse in the sequence of pulses and increasing the current level of each pulse in the sequence of pulses from the immediately preceding pulse by a second current increment. The method includes determining that the second evocation pulse from the sequence of pulses evokes the second muscular response.

19 Claims, 9 Drawing Sheets

Related U.S. Application Data

(60) Provisional application No. 62/592,275, filed on Nov. 29, 2017, provisional application No. 62/521,268, filed on Jun. 16, 2017.

(51) Int. Cl.
*A61B 5/388* (2021.01)
*A61N 1/36* (2006.01)
*G16H 20/30* (2018.01)

(52) U.S. Cl.
CPC ......... *A61N 1/36017* (2013.01); *G16H 20/30* (2018.01); *A61B 5/7264* (2013.01); *A61B 5/746* (2013.01)

(56) References Cited

U.S. PATENT DOCUMENTS 4,305,402 A 12/1981 Katims
4,863,265 A 9/1989 Flower et al.
4,934,377 A 6/1990 Bova et al.
5,024,228 A 6/1991 Goldstone et al.
5,139,028 A 8/1992 Steinhaus et al.
5,184,615 A 2/1993 Nappholz et al.
5,284,154 A 2/1994 Vickers et al.
5,313,956 A 5/1994 Knutsson et al.
5,662,105 A 9/1997 Tien
5,797,854 A 8/1998 Hedgecock
5,825,936 A 10/1998 Clarke et al.
5,827,195 A 10/1998 Lander
5,916,179 A 6/1999 Sharrock
6,067,467 A 5/2000 John
6,304,772 B1 10/2001 Taha et al.
6,391,024 B1 5/2002 Sun et al.
6,535,767 B1 3/2003 Kronberg
6,556,861 B1 4/2003 Prichep
6,634,043 B2 10/2003 Lamb et al.
6,725,086 B2 4/2004 Marinello
6,985,833 B2 1/2006 Shambroom et al.
7,174,206 B2 2/2007 Frei et al.
7,216,001 B2 5/2007 Hacker et al.
7,234,180 B2 6/2007 Horton et al.
7,286,871 B2 10/2007 Cohen et al.
7,512,439 B1 3/2009 Farazi
7,522,953 B2 4/2009 Kaula et al.
7,620,453 B1 11/2009 Propato et al.
7,628,757 B1 12/2009 Koh
7,628,761 B2 12/2009 Gozani et al.
7,806,862 B2 10/2010 Molnar
7,904,160 B2 3/2011 Brodnick et al.
8,055,349 B2 11/2011 Gharib et al.
8,108,039 B2 1/2012 Saliga et al.
8,255,045 B2 8/2012 Gharib et al.
8,386,025 B2 2/2013 Hoppe
8,440,903 B1 5/2013 Farris, III
8,515,530 B2 8/2013 Warner et al.
8,538,512 B1 9/2013 Bibian et al.
8,538,539 B2 9/2013 Pothier et al.
8,568,331 B2 10/2013 Bertagnoli et al.
8,591,431 B2 11/2013 Calancie et al.
8,731,654 B2 5/2014 Johnson et al.
8,740,783 B2 6/2014 Gharib et al.
8,812,116 B2 8/2014 Kaula et al.
8,903,487 B1 12/2014 Fischell et al.
8,965,520 B2 2/2015 Botros et al.
8,989,866 B2 3/2015 Gharib et al.
9,084,551 B2 7/2015 Brunnett et al.
9,211,074 B2 12/2015 Johnson et al.
9,332,918 B1 5/2016 Buckley et al.
9,579,037 B2 2/2017 Brunnett et al.
9,585,618 B2 3/2017 Leschinsky et al.
9,681,880 B2 6/2017 Neubardt et al.
9,700,228 B2 7/2017 Gharib et al.
9,743,853 B2 8/2017 Kelleher et al.
9,743,884 B2 8/2017 Rasmussen
9,744,356 B2 8/2017 Botros et al.
10,327,664 B2 6/2019 Kurtz et al.
10,342,443 B2 7/2019 Johnson et al.
10,376,167 B2 8/2019 Mahon et al.
10,391,012 B2 8/2019 Stashuk et al.
11,083,387 B2 8/2021 Mahon et al.
11,197,640 B2 12/2021 Johns et al.
11,684,533 B2 6/2023 Stashuk et al.
11,701,047 B2 7/2023 O'Brien et al.
11,963,775 B2 4/2024 Johns et al.
2002/0042563 A1 4/2002 Becerra et al.
2002/0183605 A1 12/2002 Devlin et al.
2003/0052775 A1 3/2003 Shambroom et al.
2003/0083719 A1 5/2003 Shankar et al.
2003/0125777 A1 7/2003 Ding et al.
2003/0176799 A1 9/2003 Beatty et al.
2004/0010303 A1 1/2004 Bolea et al.
2004/0122482 A1 6/2004 Tung et al.
2005/0075578 A1 4/2005 Gharib et al.
2005/0085866 A1 4/2005 Tehrani
2005/0101878 A1 5/2005 Daly et al.
2005/0119711 A1 6/2005 Cho et al.
2005/0228306 A1 10/2005 Kurtz
2005/0228654 A1 10/2005 Prieto et al.
2005/0261559 A1 11/2005 Mumford et al.
2005/0277826 A1 12/2005 Dunseath, Jr.
2005/0278001 A1 12/2005 Qin et al.
2006/0025702 A1 2/2006 Sterrantino et al.
2006/0052845 A1 3/2006 Zanella
2006/0173510 A1 8/2006 Besio et al.
2006/0178593 A1 8/2006 Neubardt et al.
2006/0241562 A1 10/2006 John et al.
2006/0276704 A1 12/2006 Mcginnis et al.
2007/0016097 A1 1/2007 Farquhar et al.
2007/0135722 A1 6/2007 Lin
2007/0192960 A1 8/2007 Jackson
2007/0225674 A1 9/2007 Molnar et al.
2007/0282217 A1 12/2007 Mcginnis et al.
2008/0033511 A1 2/2008 Dobak
2008/0051844 A1 2/2008 Brodnick et al.
2008/0167574 A1 7/2008 Farquhar
2008/0221473 A1 9/2008 Calancie et al.
2008/0269835 A1 10/2008 Carlson et al.
2008/0300655 A1 12/2008 Cholette
2009/0033486 A1 2/2009 Costantino
2009/0048531 A1 2/2009 Mcginnis et al.
2009/0054758 A1 2/2009 Dunseath
2009/0054804 A1 2/2009 Gharib et al.
2009/0069027 A1 3/2009 Brock et al.
2009/0082691 A1 3/2009 Denison et al.
2009/0124869 A1 5/2009 Hu et al.
2009/0143693 A1 6/2009 Ye et al.
2009/0177112 A1 7/2009 Calancie et al.
2009/0247893 A1 10/2009 Lapinlampi et al.
2010/0010367 A1 1/2010 Foley et al.
2010/0036211 A1 2/2010 La Rue et al.
2010/0042012 A1 2/2010 Alhussiny
2010/0130834 A1 5/2010 ViertiÖ-oja et al.
2010/0156376 A1 6/2010 Fu et al.
2010/0198099 A1 8/2010 Murphy et al.
2010/0274144 A1 10/2010 Hu et al.
2010/0312124 A1 12/2010 Johnson et al.
2010/0317989 A1 12/2010 Gharib et al.
2011/0054346 A1 3/2011 Mrva et al.
2011/0224570 A1 9/2011 Causevic
2011/0224988 A1 9/2011 Mahajan et al.

(56) References Cited

U.S. PATENT DOCUMENTS

2011/0230785 A1 9/2011 Higgins et al.
2011/0279676 A1 11/2011 Terada et al.
2011/0295142 A1 12/2011 Chakravarthy et al.
2012/0065536 A1 3/2012 Causevic et al.
2012/0095360 A1 4/2012 Runney et al.
2012/0136276 A1 5/2012 Johnson et al.
2012/0150063 A1 6/2012 Rea
2012/0165690 A1 6/2012 Chen et al.
2012/0197153 A1 8/2012 Kraus et al.
2012/0313757 A1 12/2012 Volpi et al.
2013/0024524 A1 1/2013 Graff et al.
2013/0035606 A1 2/2013 Wichner
2013/0116544 A1 5/2013 Rey et al.
2013/0138356 A1 5/2013 Nierenberg et al.
2013/0190599 A1 7/2013 Wyeth et al.
2013/0204156 A1 8/2013 Hampton et al.
2013/0245422 A1 9/2013 D'arcy et al.
2013/0245424 A1 9/2013 Decharms
2013/0245722 A1 9/2013 Ternes et al.
2013/0267874 A1 10/2013 Marcotte et al.
2014/0020178 A1 1/2014 Stashuk et al.
2014/0121555 A1 5/2014 Scott et al.
2014/0148725 A1 5/2014 Cadwell
2014/0275926 A1 9/2014 Scott et al.
2014/0276195 A1 9/2014 Papay et al.
2014/0288389 A1 9/2014 Gharib et al.
2014/0324118 A1 10/2014 Simon et al.
2015/0061758 A1 3/2015 Hsu
2015/0088030 A1 3/2015 Taylor
2015/0100104 A1 4/2015 Kiani et al.
2015/0148683 A1 5/2015 Hermanne
2015/0208934 A1 7/2015 Sztrubel et al.
2015/0257700 A1 9/2015 Fu
2015/0305640 A1 10/2015 Reinke et al.
2015/0313512 A1 11/2015 Hausman et al.
2016/0081570 A1 3/2016 Farquhar
2016/0106994 A1 4/2016 Crosby et al.
2016/0113587 A1 4/2016 Kothe et al.
2016/0128620 A1 5/2016 Iriki et al.
2016/0135705 A1 5/2016 Liu et al.
2016/0213268 A1 7/2016 Kim et al.
2016/0228018 A1 8/2016 Mahon et al.
2016/0270679 A1 9/2016 Mahon et al.
2017/0050041 A1 2/2017 Cosman
2017/0303811 A1 10/2017 Gharib et al.
2017/0347955 A1 12/2017 Rasmussen
2018/0078210 A1 3/2018 Snow et al.
2018/0140843 A1 5/2018 Kent et al.
2018/0310849 A1 11/2018 Johns et al.
2018/0360336 A1 12/2018 O'Brien et al.
2019/0321640 A1 10/2019 Carmena et al.
2020/0023198 A1 1/2020 Gribetz et al.
2020/0206496 A1 7/2020 Meng et al.
2020/0315478 A1 10/2020 Mahon et al.
2020/0398057 A1 12/2020 Esteller et al.
2022/0096022 A1 3/2022 Johns et al.
2022/0287619 A1 9/2022 Cleveland et al.
2023/0310864 A1 10/2023 Parker
2024/0268738 A1 8/2024 Johns et al.
2025/0204842 A1 6/2025 Torres

FOREIGN PATENT DOCUMENTS

CN 101309419 A 11/2008
CN 201185940 Y 1/2009
CN 102361590 A 2/2012
CN 102368951 A 3/2012
CN 102481107 A 5/2012
CN 102594472 A 7/2012
CN 102824170 A 12/2012
CN 102883775 A 1/2013
CN 103908248 A 7/2014
CN 104411234 A 3/2015
JP S51154986 U 12/1976
JP S59193403 U 6/1983
JP S5922106 A 2/1984
JP S5922106 U 2/1984
JP S59193403 A 11/1984
JP H04253843 A 9/1992
JP H06508288 A 9/1994
JP H06277189 A 10/1994
JP H1176185 A 3/1999
JP 2003131668 A 5/2003
JP 2004517669 A 6/2004
JP 2005073223 A 3/2005
JP 2005519646 A 7/2005
JP 2007185326 A 7/2007
JP 2009011896 A 1/2009
JP 2009502424 A 1/2009
JP 2009071387 A 4/2009
JP 2009118969 A 6/2009
JP 2009534159 A 9/2009
JP 2010104586 A 5/2010
JP 2012505707 A 3/2012
JP 2012529344 A 11/2012
JP 2012236007 A 12/2012
JP 5466389 B2 4/2014
JP 2017502711 A 1/2017
JP 2020511276 A 4/2020
WO 2001074248 A1 10/2001
WO 03005887 A2 1/2003
WO 2003000128 A2 1/2003
WO 2003005887 A2 1/2003
WO 2006072050 A2 7/2006
WO 2006084193 A2 8/2006
WO 2010144200 A1 12/2010
WO 2011045936 A1 4/2011
WO 2013166157 A1 11/2013
WO 2015048822 A1 5/2015
WO 2016179191 A1 11/2016
WO 2018232365 A1 12/2018
WO 2022192569 A1 9/2022

OTHER PUBLICATIONS

"NeuroStream—Intraoperative Monitoring Interpreting Physician Access" [online][retrieved Apr. 21, 2010). Retrieved from the Internet at Hyperlink "http://www.neurostream.us/solutionstelemedicine.iso?nav=1".

"NeuroStream—IOM and Neurophysiological Monitoring Software" [online][retrieved Apr. 21, 2010). Retrieved from the Internet at Hyperlink "http://www.neurostream.us/solutionscaseExecution.iso?nav=1".

"NeuroStream—Software for Intraoperative Monitoring Scheduling" [online][retrieved Apr. 21, 2010). Retrieved from the Internet at Hyperlink h http://www.neurostream.us/solutionsschedulina.iso?nav= 1.

AMSCO 3085 SP Surgical Table Sales Brochure, STERIS Corporation; Apr. 2006, 16 pages.

Baumann, et al., Intraoperative SSEP Detection of Ulnar Nerve Compression or Ischemia in an Obese Patient: A Unique Complication Associated With a Specialized Spinal Retraction System; Archives of Physical Medicine and Rehabilitation, vol. 81.

Ben-David, et al., Prognosis of Intraoperative Brachial Plexus Injury: A Review of 22 cases, British Journal of Anaesthesia, vol. 79, No. 4, Oct. 1997, pp. 440-445.

Bizzarri, et al., Iatrogenic Injury to the Long Thoracic Nerve: An Underestimated Cause of Morbidity After Cardiac Surgery, Texas Heart Institute Journal, vol. 28, No. 4, Jan. 2001, pp. 315-317.

Chung, Induk, et al., "Upper-limb somatosensory evoked potential monitoring in lumbosacral spine surgery: a prognostic marker for position-related ulnar nerve injury." The Spine Journal 9.4 (Apr. 2009): 287-295.

Crum, et al. "Peripheral nerve stimulation and monitoring during operative procedures." Muscles & nerve 35.2: 159-170. (Year: 2007).

Crum, et al. "intraoperative peripheral nerve stimulation and recording." Handbook of Clinical Neurophysiology 8: 364-370. (Year: 2008).

(56) References Cited

OTHER PUBLICATIONS

China National Intellectual Property Adminsitration, "Office Action," Chinese Application No. 202110429148.7, Nov. 23, 2023.
European Patent Office, "Communication Pursuant to Article 94(3) EPC," European Application No. 18771706.1, mailed Jul. 4, 2023.
European Patent Office, "Extended European Search Report," European Application No. 23188630.0, Sep. 5, 2023.
Extended European Search Report issued in European Application No. 13784125.0, mailed on Dec. 9, 2015, 8 pages.
Extended European Search Report issued in European Application No. 16789949.1, mailed on Dec. 4, 2018, 7 pages.
Fishel, et al., Case Report: Postoperative Injuries of Upper Limb Nerves, The Clinical Journal of Pain, vol. 6, No. 2, Jun. 1990, pp. 128-130.
Graham, et al., Brachial Plexus Injury After Median Sternotomy, Journal of Neurology, Neurosurgery, and Psychiatry, vol. 44, Jul. 1981, pp. 621-625.
Hickey et al., "Intraoperative Somatosensory Evoked Potential Monitoring Predicts Peripheral Nerve Injury During Cardiac Surgery", Anesthesiology 78(1), 29-35 (1993).
Hongxuan Zhang et al., "Intraoperative Neurological Monitoring," vol. 25, No. 4, Jul. 1, 2006 (Jul. 1, 2006), pp. 39-45.
International Search Authority, "Search Report and Written Opinion," International Application No. PCT/US/2023/029024, Dec. 15, 2023.
International Search Report and Written Opinion for Application No. PCT/US2014/064433, dated Apr. 4, 2015, 10 pages.
International Search Report and Written Opinion for PCT Application No. PCT/US2010/034076, dated Jul. 9, 2010, 8 pages.
International Search Report and Written Opinion received for PCT Application No. PCT/US2016/030605, mailed on Aug. 8, 2016, 8 pages.
Winfree, et al., Intraoperative Positioning Nerve Injuries, Surgical Neurology, vol. 63, No. 1, Jan. 2005, pp. 5-18.
Japan Patent Office, "Office Action," Japanese Application No. 2022191709, mailed Nov. 14, 2023.
Jellish, et al., Hands-Up Positioning During Asymmetric Sternal Retraction for Internal Mammary Artery Harvest: A Possible Method to Reduce Brachial Plexus Injury, Anesthesia and Analgesia, vol. 84, No. 2, Feb. 1997, pp. 260-265.
Kamel et al., "The Use of Sematosensory Evoked Potentials to Determine the Relationship Between Patient Positioning and Impending Upper Extremity Nerve Injury During Spine Surgery: A Retrospective Analysis", Anesth Analg 102(5), 1538-1542 (2006).
Labrom et al., "Clinical Usefulness of Somatosensory Evoked Potentials for Detection of Brachial Plexopathy Secondary to Malpositioning in Scoliosis Surgery", Spine 30(18), 2089-2093 (2005).
Makarov, et al., Intraoperative SSEP Monitoring During External Fixation Procedures in the Lower Extremities, Journal of Pediatric Orthopaedics, vol. 16, No. 2, Mar./Apr. 1996, pp. 155-160.
Makarov, et al., Monitoring Peripheral Nerve Function During External Fixation of Upper Extremities, Journal of Pediatric Orthopaedics, vol. 17, No. 5, Sep./Oct. 1997, pp. 663-667.
Makeig, et al., Mining event-related brain dynamics, Trends in Cognitive Sciences. vol. 8, No. 5, May 2004, pp. 204-210.
Nagda, et al., Neer Award 2005: Peripheral Nerve Function During Shoulder Arthoplasty Using Intraoperative Nerve Monitoring, Journal of Shoulder and Elbow Surgery, vol. 16, No. 3, Supplement, May-Jun. 2007, 7 pages.
Posta, Jr., et al., Neurologic Injury in the Upper Extremity After Total Hip Arthroplasty, Clinical Orthopaedics and Related Research, vol. 345, Dec. 1997, pp. 181-186.
Prielipp, et al., Ulnar Nerve Pressure: Influence of Arm Position and Relationship to Somatosensory Evoked Potentials, Anesthesiology, vol. 91, No. 2, Aug. 1999, 10 pages.
Supplemental Partial European Search Report for Application No. EP 14 86 1025, dated Jun. 26, 2017.
Warner et al. (Dec. 1994) "Ulnar Neuropathy. Incidence, Outcome, and Risk Factors in Sedated or Anesthetized Patients", Anesthesiology, 81(6):1332-1340.
Calancie, Blair et al., "Isoflurane-induced attenuation of motor evoked potentials caused by electrical motor cortex stimulation during surgery," J Neurosurg, vol. 74, No. 6, Jun. 1991, 897-904.
Calencie, Blair et al., "Threshold-level repetitive transcranial electrical stimulation for intraoperative monitoring of central motor conduction," J Neurosurg (Spine 1), vol. 95, No. 2, Oct. 2001, 161-168.
Conde, Virginia et al., "The non-transcranial TMS-evoked potential is an inherent source of ambiguity in TMS-EEG studies," NeuroImage, vol. 185, 2019, 300-312.
Deletis, V. et al., "Facilitation of motor evoked potentials by somatosensory afferent stimulation," Electroencephalography and clinical Neurophysiology, vol. 85, No. 5, May 1992, 302-310.
Yamamoto Yusuke et al: "Tetanic stimulation of the peripheral nerve augments motor evoked potentials by re-exciting spinal anterior horn cells", Journal of Clinical Monitoring and Computing, vol. 36, No. 1, Jan. 9, 2021, pp. 259-270.
Haghighi, Sivanash S. et al., "Effect of Desflurane Anesthesia on Transcortical Motor Evoked Potenitals," Journal of Neurosurgical Anesthegiology, vol. 8, No. 1, 1996, 47-51.
Hosel Katarina et al, "Facilitation of Motor Evoked Potentials in Response to a Modified 30 Hz Intermittent Theta-Burst Stimulation Protocol in Healthy Adults", Dec. 12, 2021, vol. 11, No. 12, p. 1640.
International Bureau, "International Preliminary Report on Patentability," for PCT Patent Application No. PCT/US2023/022575, Nov. 28, 2024.
Ito, Zenya et al., "Usefulness of multi-channels in interaoperative spinal cord monitoring: multi-center study by the monitoring committee of the Japanese Society for Spine surgery and related research," Eur Spine J, vol. 22, No. 8, Apr. 2013, 1891-1896.
Journee, H.-L. et al., "Conditioning stimulation techniques for enhancement of transcranially elicited evoked motor responses," Clinical Neurophysiology, vol. 37, No. 6, Nov. 2007, 423-430.
Kothbauer, Karl F. et al., "Motor-evoked potential monitoring for intramedullary spinal cord tumor surgery: correlation of clinical and neurophysiological data in a series of 100 consecutive procedures," Neurosurgical Focus, vol. 4, No. 5, Apr. 1998.
Legatt, Alan D. et al., "Guideline on Transcranial Electrical Stimulation Motor Evoked Potential (TES-MEP) Monitoring," Journal of Clinical Neurophysiology, vol. 33, No. 1, Feb. 2016, 42-50.
Lima, Ernesto et al., "Linked Quadri-Polar (LQP-TceMEP) Technique during a scoliosis procedure: a case report," Neurlological Monitoring Associates, LLC, 2019.
Lo, YL et al., "Intra-operative monitoring in scoliosis surgery with multi-pulse cortical stimuli and desflurane anesthesia," Spinal Cord, vol. 42, No. 6, 2004, 342-345.
MacDonald, D.B. et al., "Intraoperative motor evoked potential monitoring—A position statement by the American Society of Neruophysiological Monitoring," Clinical Neurophysiology, vol. 124, No. 12, Sep. 2013, 2291-2316.
Masuda, Keisuke et al., "Monophasic transcranial constant-current versus constant-voltage stimulation of motor-evoked potentials during spinal surgery," Scientific Reports, vol. 9, No. 3773, Mar. 2019.
Merton, P. A. et al., "Stimulation of the cerebral cortex in the intact human subject," Nature, vol. 285, No. 5762, Mar. 1980, 227.
Ohashi, Masayuki et al., "False-negative transcranial motor evoked potentials (TcMEPs) during surgery for congenital lumbar kyphoscoliosis: a case report," vol. 3, No. 17053, Sep. 2017.
Schwartz, Stephanie L. et al., ""Quadripolar" Transcranial Electrical Stimulation for Motor Evoked Potentials," Journal of Clinical Neurophysiology, vol. 39, No. 1, Jan. 2022, 92-97.
Shigematsu, Hideki et al., "Higher success rate with transcranial electrical stimulation of motor-evoked potentials using constant-voltage stimulation . . . ," The Spine Journal, vol. 17, No. 10, Oct. 2017, 1472-1479.
Szelenyi, Andrea et al., "Transcranial electric stimulation for intraoperative motor evoked potential monitoring: Stimulation parameters and elctrode montages," Clnical Neurophysiology, vol. 118, No. 7, Jul. 2007, 1586-1595.

(56) References Cited

OTHER PUBLICATIONS

Thirumala, Parthasarathy D. et al., "Alarm criteria for motor evoked potentials," Nuerology India, vol. 65, No. 4, 2017, 708-715.
Thirumala, Parthasarathy D. et al., "Somatosensory-evoked potential monitoring during instrumented scoliosis corrective procedures: validity revisited," The Spine Journal, vol. 14, No. 8, Aug. 2014, 1572-1580.
China National Intellectual Property Administration, "Decision of Rejection," for Chinese Patent Application No. 202110429148.7, Jun. 29, 2024.
China National Intellectual Property Administration, "Second Office Action," for Chinese Patent Application No. 202110429148.7, Apr. 20, 2024.
European Patent Office, "Communication under Rule 71(3) EPC," for European Patent Application No. 18771706.1, May 2, 2024.
Japan Patent Office, "Notice of Allowance," for Japanese Patent Application No. 2022-191709, May 7, 2024.
Doemges, et al., "Changes in the Stretch Reflex of the Human First Dorsal Interosseous Muscle During Different Tasks," Journal of Physiology, 1992, pp. 563-573, vol. 447.
The International Bureau of WIPO, "International Preliminary Report on Patentability," International Application No. PCT/US2022/019798, Sep. 21, 2023.
European Patent Office acting as International Searching Authority, "Search Report and Written Opinion," International Application No. PCT/US2022/019798, Jul. 6, 2022.
European Patent Office, "Communication Pursuant to Article 94(3) EPC," European Application No. 20192956.9, Mar. 27, 2024.
Cecotti, Hubert. "A time frequency convolutional neural network for the offline classification of steady-state visual evoked potential responses." Pattern Recognition Letters 32.8 (2011): 1145-1153. (Year: 2011),.
Japan Patent Office, "Notice of Refusal," for Japanese Patent Application No. 2023-553052, Dec. 9, 2025.
S. Xue, X. Geng and D. Li, "Feature Extraction and Classification of EEG Signal Based on Deep Learning," 2022 International Conference on Intelligent Transportation, Big Data & Smart City (ICITBS), Hengyang, China, 2022, pp. 123-126, (Year: 2022).

SYSTEMS, METHODS, AND DEVICES FOR DETECTING THE THRESHOLD OF NERVE-MUSCLE RESPONSE USING VARIABLE FREQUENCY OF STIMULATION

RELATED APPLICATIONS

This application is a continuation of U.S. patent application Ser. No. 16/010,157, filed on Jun. 15, 2018, which claims priority to U.S. Provisional Application No. 62/521,268, filed on Jun. 16, 2017, and U.S. Provisional Application No. 62/592,275, filed on Nov. 29, 2017, the entirety of each is incorporated by reference herein.

FIELD

The present technology generally relates to the field of clinical neurophysiology. More specifically it relates generally to systems, devices, methodology, rules, operations, calculations and/or steps used for stimulator control capable of more accurately finding stimulation thresholds to estimate nerve health, integrity of adjacent structures, or nerve proximity, for instance while developing a surgical corridor.

BACKGROUND

Various types of intraoperative monitoring (TOM) are utilized during medical surgeries. Such TOM includes monitoring to evaluate the integrity of aspects of the nervous system or structures adjacent components of the nervous system. One type of TOM involves determining stimulation threshold levels, which typically involve identifying the minimum stimulation required to elicit muscle activation. Embodiments described herein generally relate to improved systems, devices and methods for detecting the stimulation threshold of a nerve-muscle response.

SUMMARY

By using graded electrical stimulation the threshold stimulation intensity of a motor nerve can be measured during surgery. For example, in an automated triggered electromyography system, it may be desired to determine a stimulation current threshold associated with a compound muscle action potential (CMAP) or partial compound motor action potential (PCMAP) that meets certain predetermined criteria. The CMAP or PCMAP is composed of multiple motor units (MU) that have different stimulation thresholds. By gradually increasing the stimulus intensity from sub-threshold to maximal values some or all MUs in the muscle or myotome are activated. The stimulation median threshold range from the first MU being evoked to 95% of MUs being evoked may be 7.6 mA (5.4-11.5). Thresholds are used to estimate proximity of the nerve to the simulator and the health of the nerve in responding to stimuli or the integrity of anatomical features adjacent to nerves. Multiple types of methods, including computer implemented methods, are used to find stimulation thresholds primarily aimed at accuracy of threshold finding, speed of threshold finding or finding thresholds over multiple muscles or myotomes to triangulate where the stimulator is in relation to the nerve or nerves in question.

While many approaches utilize algorithms that are useful, they suffer from several issues. Many times, the surgical team is not interested in determining the threshold of multiple myotomes or triangulating the stimulator placement. They are much more interested in locating the closest nerve or the nerve with the lowest threshold which is therefor most at risk. In addition, these methods do not always take into account the variability in likelihood of any particular MU responding to a single stimulation intensity which can produce variability in the threshold level when activating PCMAPs.

In addition, during surgery, muscular blockade is often given. While strategies are available for determining the degree of blockade present such as the most popular method of measuring the degree of muscular blockade is the train of four (TOF), this technique has limited accuracy and is often neglected. Consequently, threshold testing may be inaccurate since the muscular blockade blunts the muscular response to stimulation.

While high frequency stimulation (10-20 Hz) of a nerve and attached muscle will condition the neuro-muscular junction to produce a response even in the presence of partial muscular blockade, persistent stimulation at those frequencies may lead to muscular tetany and confound results. Stimulation at lower frequencies (e.g. 1-5 Hz) may not provide adequate conditioning and therefore fail to provide an accurate response from the muscle. Similarly, stimulation intensities that vary dramatically while trying to 'zero in' on the threshold such as used in a bisecting algorithm may not provide adequate conditioning for an accurate response, as fewer stimuli occur close to the threshold intensity. These systems also do not account for variability in PCMAP response that can occur when the threshold is approached from higher or lower stimulation intensities.

Certain methods may also require low frequencies, such that they are below levels which would induce tetany. In addition, since lower thresholds often suggest nerve proximity, which is of primary interest to the user, stimulation patterns that update more quickly for lower stimulation thresholds is preferred but not always available. Failure to interrogate the muscular response over the entire expected range of responses to stimulation may fail to confirm an accurate threshold when spurious responses are present or fail to adequately show an absence of response throughout the expected range when none is present.

In some automated Electromyography (EMG) systems, a transient noise disturbance, spontaneous EMG spike or burst, or other anomaly may be mistaken for an electrically elicited CMAP and lead to an erroneously identified threshold (e.g., a false positive).

Also, some automated EMG systems may, under some conditions, approach a stimulation threshold from above and, under other conditions, approach a stim threshold from below. This method may lead to variability in a determined threshold because of the range of stimulation required to elicit the first MU response and the maximal CMAP can differ by more than 7 mA. By approaching the stimulation threshold from below the stimulation threshold for the first MUs that comprise the CMAP, the threshold could be 7 mA less than approaching the stimulation threshold from above.

Non-limiting example embodiments disclosed herein address at least some of the previously described drawbacks. The example embodiments provide a simple and rapid way to obtain thresholds that update quickly when at critical threshold levels.

According to some embodiments, a method for determining a lowest stimulation threshold current level in a group of channels of a neuromonitoring device, wherein each channel is associated with one or more muscles, includes stimulating, by delivering stimulation signals, tissue at a current level from within a predetermined range of current levels as a sequence of pulses delivered at a frequency. The stimulating includes increasing the current level of each pulse in the sequence of pulses from an immediately preceding pulse by a first current increment. The method includes determining that a first evocation pulse from the sequence of pulses evokes a first muscular response. The method includes stimulating the tissue with a second evocation pulse from the sequence of pulses to evoke a second muscular response. The stimulating includes decreasing the frequency of the delivery of each pulse in the sequence of pulses and increasing the current level of each pulse in the sequence of pulses from the immediately preceding pulse by a second current increment. The method also includes determining that the second evocation pulse from the sequence of pulses evokes the second muscular response.

In some embodiments, the second current increment is the same as the first current increment. In some embodiments, the determining that the first evocation pulse from the sequence of pulses evokes the first muscular response further includes storing a first current level of the first evocation pulse. In some embodiments, the determining that the first evocation pulse evokes the first muscular response includes receiving a first signal representing the first muscular response and the determining that the second evocation pulse evokes the second muscular response includes receiving a second signal representing the second muscular response.

In some embodiments, the method includes comparing the first signal to the second signal, determining that the first signal matches the second signal, and displaying a first current level of the first evocation pulse.

In some embodiments, the method includes comparing the first signal to the second signal, determining that the first signal does not match the second signal, and stimulating the tissue with a third evocation pulse from the sequence of pulses to evoke a third muscular response. The stimulating includes increasing the frequency of the delivery of each pulse in the sequence of pulses and increasing the current level of each pulse in the sequence of pulses from the immediately preceding pulse.

In some embodiments, the method includes continuing to deliver an evocation pulse until a maximum stimulus current level within the predetermined range of current levels is reached. In some embodiments, the presence or absence of muscular responses from each of the channels in the group of channels is determined.

According to some embodiments, a method for determining a stimulation threshold includes determining a threshold by delivering a plurality of stimulation pulses to determine a first current level that generates a predetermined response. The method can include continuing to delivery at least one stimulation pulse at least the same current level to generate another predetermined response.

According to some embodiments, a method of medical treatment includes performing a medical procedure using any apparatus and method described herein.

According to some embodiments, a method for determining a stimulation threshold current level includes stimulating, by delivering stimulation pulses via at least one electrode, tissue at a current level as a sequence of pulses. The stimulating includes increasing the current level of each pulse in the sequence of pulses from an immediately preceding pulse. The method includes determining that a first evocation pulse from the sequence of pulses evokes a first muscular response. The method includes stimulating the tissue with a second evocation pulse from the sequence of pulses to evoke a second muscular response. The stimulating may include decreasing the frequency of the delivery of each pulse in the sequence of pulses. The stimulating may include delivering the second evocation pulse at the same or higher current level relative to the immediately preceding pulse. The method also includes determining that the second evocation pulse from the sequence of pulses evokes the second muscular response.

According to some embodiments, a method for determining a lowest stimulation threshold current level in a group of channels of a neuromonitoring device, wherein each channel is associated with one or more muscles, includes stimulating tissue within a predetermined range of current levels as a sequence of pulses delivered at a frequency by delivering stimulation signals. The sequence of pulses includes a first pulse delivered at a first current level within the predetermined range of current levels, and a second pulse delivered at a second current level within the predetermined range of current levels. The first pulse may be delivered immediately preceding the second pulse. The second current level may be higher than the first current level. The method may include determining that the second pulse evokes a muscular response that is similar to the first response. The method may also include stimulating the tissue with a third pulse from the sequence of pulses to evoke a third muscular response. The third pulse may be delivered at a third current level that is higher than the second current level. The method may include determining that the third pulse evokes the third muscular response that is similar to the first and second response.

In some embodiments, the stimulating further comprises decreasing the frequency of the delivery of each pulse in the sequence of pulses, and increasing the current level of the third pulse by an amount that is greater than a difference between the first current level and the second current level. In some embodiments, the determining that the second pulse from the sequence of pulses evokes the first muscular response further includes storing the second current level. In some embodiments, the determining that the second pulse evokes a muscular response that is similar to the first muscular response includes receiving a first signal representing the first muscular response and the determining that the third pulse evokes a muscular response that matches the second muscle response includes receiving a second signal representing the second muscular response.

In some embodiments, the method includes comparing the first signal with the second signal, determining that the first signal matches the second signal, and displaying the second current level of the second pulse. In some embodiments, the method includes comparing the first signal with the second signal, determining that the first signal does not match the second signal, and stimulating the tissue with a fourth pulse from the sequence of pulses to evoke a third muscular response. The stimulating may include increasing the frequency of the delivery of each pulse in the sequence of pulses. The stimulating may also include increasing the current level of each pulse in the sequence of pulses from the immediately preceding pulse.

In some embodiments, the method includes continuing to deliver a pulse until a maximum stimulus current level within the predetermined range of current levels is reached. In some embodiments, the presence or absence of muscular responses from each of the channels in the group of channels is determined.

According to some embodiments, a method for performing neurophysiologic assessments includes determining the lowest stimulation threshold current level in a group of channels of a neuromonitoring device, where each channel is associated with one or more muscles. Determining the lowest stimulation threshold current level (ST) includes delivering stimulation signals within tissue and monitoring muscular responses on the group of channels to determine when the stimulation signals evoke a significant muscular response from any of the channels. The stimulation signals may be delivered within a specific range of possible current levels as a sequence of pulses delivered at a frequency. The current level of each pulse may be increased from an immediately preceding pulse by an increment until the current level required to evoke a significant muscular response is determined. Upon determining the stimulus threshold current level, the frequency of the stimulation may be reduced and the increment between stimulus current levels may be increased. The method further includes continuing to deliver stimulation pulses until a maximal stimulus current level within the specific range of possible current levels is reached. The presence or absence of responses from any other channels are determined and the entire process is then repeated to determine any change in stimulus threshold current level (ST) over time.

In some embodiments, the muscular response is detected by an EMG sensor and the stimulation threshold current level is determined when the muscular response reaches a pre-determined peak-to-peak voltage. The muscular response may be detected by an MMG (Mechanomyography) sensor and the stimulation threshold current level may be determined. In some embodiments, the predetermined peak-to-peak voltage from within the range of 20 u V to 100 u V. In some embodiments, the stimulus current levels are displayed to the user on a user interface. In some embodiments, the stimulation threshold current level is displayed to the user on a user interface.

In some embodiments, the muscle responses to the stimuli are displayed to the user on a user interface. In some embodiments, the increment is 0.25 mA or 0.5 mA and the frequency is 20 Hz. In some embodiments, the increased increment is 2.0 mA and the reduced frequency is 5 Hz. In some embodiments, a specific range of possible current levels has a maximum of 20 mA.

In some embodiments, a method can assess the presence of a nerve relative to at least one probe or surgical tool being introduced towards at least one region of a patient's spine or peripheral nerve site In some embodiments, a device, apparatus or system for intraoperative monitoring can include a surgical tool and one or more components that deliver stimulation signals within tissue and monitor muscular responses on a group of channels to determine when the stimulation signals evoke a significant muscular response from any of the channels.

According to some embodiments, a method for assessing the presence of a nerve relative to at least one probe or surgical tool being introduced towards at least one region of a patient's spine or peripheral nerve site includes emitting a stimulus signal from an electrode disposed on a probe or surgical tool as said probe or tool is introduced towards any aspect of a vertebral body, an intervertebral disc of a patient's spine or placed near any peripheral motor nerve. The method includes electromyographically monitoring muscles coupled to said spinal nerve to determine if any predetermined neuro-muscular response is elicited by the stimulus signal. The method also includes increasing the intensity level of said stimulus signal through a predetermined range of values utilizing a variable stimulus frequency and calculating which neuro-muscular response is elicited by the lowest stimulus pulse, and if any other neuro-muscular response is elicited throughout the range. The method also includes communicating to an operator said lowest intensity level of said stimulus signal required to elicit said predetermined neuro-muscular response. The intensity level required to elicit the predetermined neuro-muscular response represents the presence of said spinal nerve within the sweep range.

In some embodiments, upon identifying said lowest intensity level of said stimulus signal required to elicit said predetermined response, the method includes continuing to emit stimulus signal for the predetermined range. The method can include continuing to emit stimulus signal for the predetermined range comprises emitting successively stronger signals within the predetermined range.

In some embodiments, the emitting of successively stronger signals within the predetermined range includes decreasing the frequency of the signal emission compared to the frequency prior to identifying the lowest intensity level required to emit the predetermined response, and/or increasing the increase in stimulus intensity compared to the frequency prior to identifying the lowest intensity level required to emit the predetermined response. In some embodiments, the stimulus signal is emitted from an electrode disposed anywhere along the length of at least one probe or surgical tool.

In some embodiments, detecting neuro-muscular responses involves detecting the neuro-muscular responses at a plurality of distally spaced apart myotome locations corresponding to each of a plurality of spinal nerves. In some embodiments, the method includes repeating the method while the intensity level of the electrical stimulus signal is restarted at its lowest level and swept through the same range. In some embodiments, the intensity and frequency of stimulation level of the stimulus signal is varied incrementally. In some embodiments, the intensity level of the stimulus signal is increased over time until it reaches the extremes of the stimulating range.

In some embodiments, the method is performed in a repeating sequence. In some embodiments, the method is repeated automatically. In some embodiments, the method is repeated under operator control. In some embodiments, communicating to said operator involves at least one of visually and audibly indicating to said operator the lowest intensity level of the stimulus signal required to elicit any said predetermined neuro-muscular response as well as all said predetermined neuro-muscular responses. In some embodiments, the method includes repeating the method thereby detecting and measuring sequential sets of neuro-muscular responses for said nerves. In some embodiments, the method includes visually indicating to said operator that said nerve is within the sweep range of at least one probe or surgical tool.

In some embodiments, the method includes audibly indicating to said operator that said spinal nerve is positioned near the distal end of the at least one probe or surgical tool. Audibly indicating to said operator involves sounding an alarm when the lowest intensity level of the stimulus signal required to elicit any said predetermined neuro-muscular response is at or below a specific predetermined stimulus intensity. The volume of the alarm is varied according to the lowest intensity level of the stimulus signal required to elicit any said predetermined neuro-muscular response. The frequency of the alarm is varied according to the lowest intensity level of the stimulus signal required to elicit any said predetermined neuro-muscular response.

In some embodiments, the method is performed on multiple myotomes. In some embodiments, a medical instrument is selected from the group consisting of implants, rods, fixation devices, disc replacements, probes, dilators, retractors, pedicle screws, pedicle screw awls, nerve stimulators, curettes, forceps, needles, micro-dissectors, rongeurs, elevators, rasps, gouges, surgical site lights and suction tubes.

DETAILED DESCRIPTION

According to implementations of the current subject matter, a system, method, device and/or computer implemented algorithm for automatically detecting the stimulation threshold of a nerve or nerves resulting in the recordable response in one or more muscles innervated by that nerve(s) is disclosed. The system, method, device and/or computer algorithm relate to determining the lowest stimulation threshold current level in a group of channels of a neuromonitoring device. Each channel may be associated with one or more muscles.

As described herein, a Stimulation Intensity (SI) refers to an electrical stimulus current level in amperage of a defined duration, typically one of 50, 100 or 200 microseconds. Stimulation threshold (ST) is defined as the lowest SI that causes a nearby or adjacent nerve to depolarize. The ST may result in recordable depolarization of one or more attached muscles. Depolarization of the muscles may be recorded via an electromyogram (EMG) or mechanomyography (MMG) using electrodes positioned on the muscle(s). The resulting EMG or MMG will show depolarization. The Interrogation Range (IR) is the range of SIs that are of interest to the user for their particular application, typically determined to include STs that disclose the relative health, proximity or structural integrity of the tissue being stimulated. The IR is pre-determined based on the particular application and/or may be customized or selected by a healthcare provider. In an exemplary embodiment, the IR may be tailored to the patient's particular situation so that several versions of IR exist with differing or the same stimulation frequency and increments. Stimulation frequency (Frequency) is the frequency at which stimuli are delivered to the tissue. Stimulation increments (Increments) are the incremental changes in stimulation intensity between subsequent stimuli.

In implementations of the current subject matter, a stimulation probe may be used to provide a stimulation pulse, which acts on one or more nearby nerves. The probe may include electrodes that provide the stimulation pulse. In some embodiments, the electrodes are placed on the patient separately from the probe. The probe may be stationary and/or may be moved along a trajectory.

Systems, devices, and methods for determining a threshold stimulation pulse according to the current subject matter may be implemented using a bottom-up approach. For example, as described in more detail herein, the stimulation pulses are applied to the patient by approaching the current threshold from below, for example, by incrementally increasing stimulation current starting from a low value. Configurations according to the current subject matter improve the accuracy and/or repeatability of the current threshold.

Figure 1:
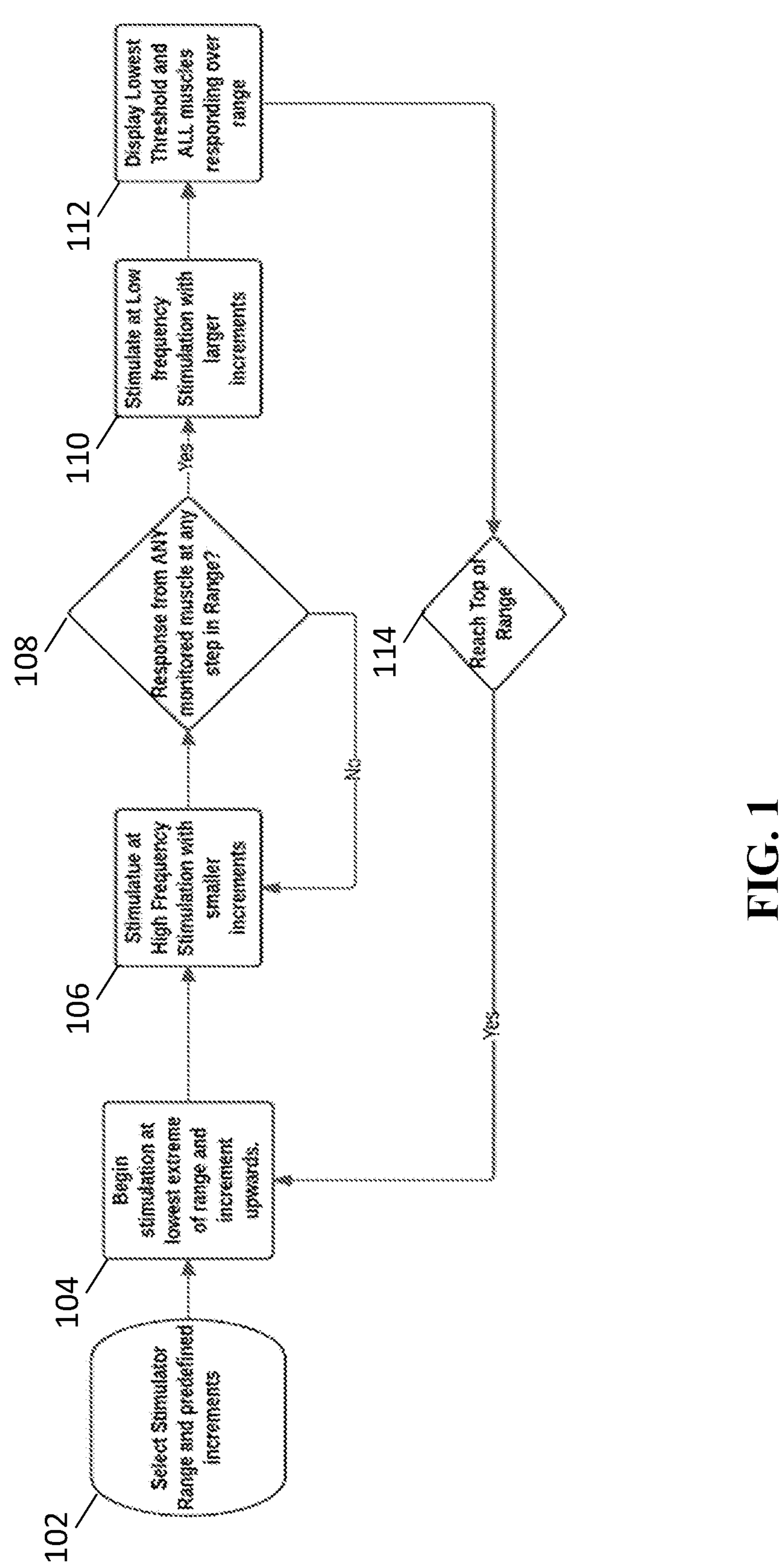
FIG. 1 shows an embodiment of a process for determining a stimulation threshold according to implementations of the current subject matter.

FIG. 1 illustrates a flowchart showing an example method 100 for determining a current threshold according to implementations of the current subject matter. At step 102, the IR, the frequency, and/or the initial current may be defined. The IR, the frequency, and/or the initial current may be defined automatically by the system and/or through inputs received by the system from the user via a user interface.

At 104, the device begins stimulation of the patient's tissue by delivering pulses at a high frequency and with a low current (e.g., SI). For example, in some embodiments, the SI may be initially set to 0.25 mA and the initial frequency may be set to 20 Hz.

Figure 2:
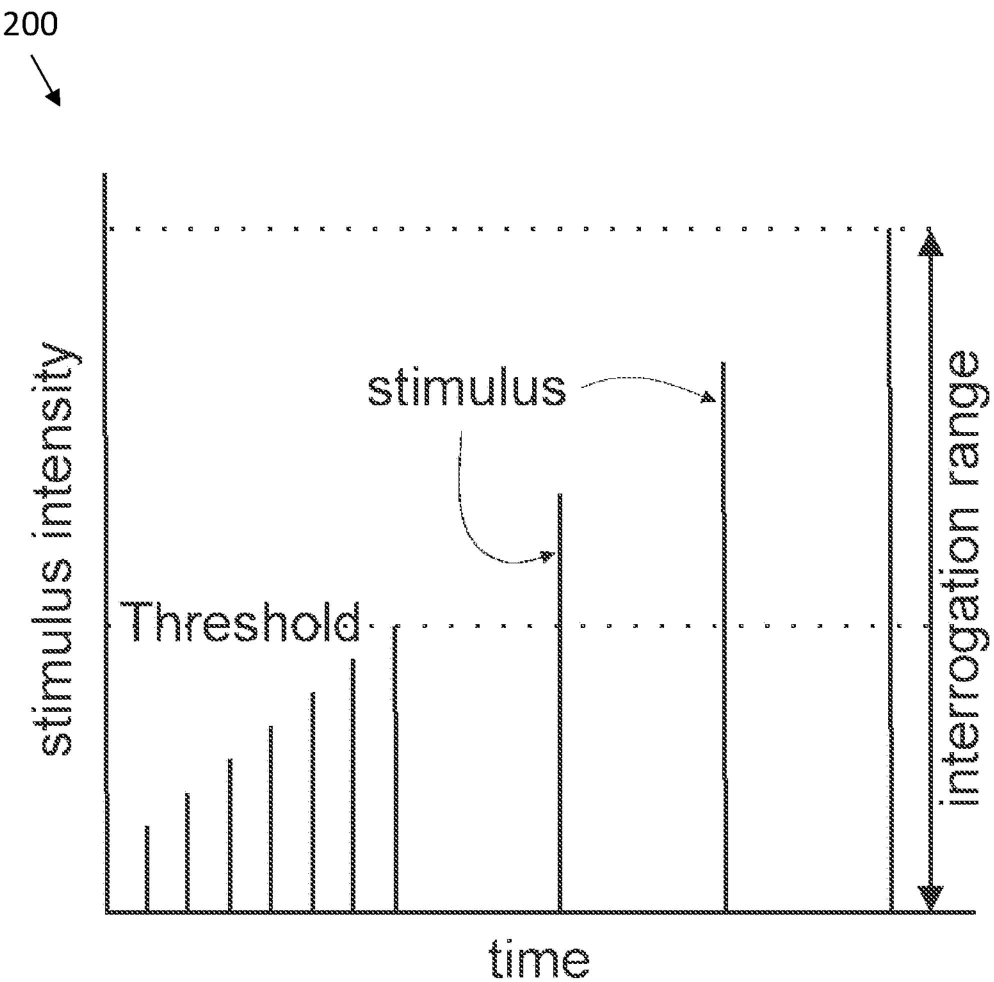
FIG. 2 shows an embodiment of a stimulation pattern according to implementations of the current subject matter.

At 106, the SI may be incrementally increased after each delivered pulse. FIG. 2 illustrates an example of a sequence of pulses in which the SI is incrementally increased after each delivered pulse. In some example embodiments, the stimulation begins at a SI of 0.25 mA at a frequency of 20 Hz. Thus, the SI may be incrementally increased, such as by 0.25 mA, after each pulse is delivered to the patient's tissue.

The system may continue to deliver stimulation pulses to the patient at the same frequency until an initial response is received by the system in response to the SI (see FIG. 2), at step 108. If no responses are received by the system in response to the SI, the system may continue to deliver stimulation pulses to the patient at step 106.

In some embodiments, ST may be detected by using the resulting EMG or MMG. ST may be determined when the resulting muscle activity reaches a pre-determined magnitude, such as a measured as a peak-to-peak voltage. In some embodiments, the predetermined magnitude is a peak-to-peak voltage from within the range of 20 u V to 100 u V. The system then shows the user the threshold, for example, on a user interface, such as at 112.

The ST may be determined from a plurality of channels, where the ST is the lowest threshold (i.e., resulting muscle activity) observed from any of the channels. Accordingly, rather than assessing each channel in a multi-channel system individually, the system may assess the muscular response on all channels, and determine the ST from lowest stimulation threshold response.

After the potential threshold is determined, the system may continue to deliver stimulation pulses to the patient. At 110, stimulation frequency is decreased and current of one or more pulses is increased. In some embodiments, the stimulation frequency is decreased to 5 Hz. In some embodiments, the increment size is increased to 2 mA. Using the decreased frequency and increased current and/or current increment, the system may continue to deliver stimulation pulses to the patient until the current levels reaches the top of the IR at 114. In some embodiments, the maximum of the IR is 20 mA. If additional muscle responses are recruited from other muscles being recorded, the user display shows the user that those muscles are within the IR. The system may then repeat the process at 102 and update the ST with each sweep until the user stops the process or the system automatically stops the process.

Changes in the ST may be descriptive of nerve health, integrity of adjacent structures, or nerve proximity, for instance while developing a surgical corridor. In some embodiments, the changes may describe at least one of pedicle integrity, nerve pathology, and spinal cord health. In certain embodiments, the disclosed system and method is useful for determining nerve proximity. For this purpose, a decrease in ST would indicate an approach of a nerve, and may indicate to a user to discontinue that particular approach trajectory. A certain ST may indicate that the probe is too near to a nerve and that nerve damage may be imminent. Accordingly, a continuous detection and update of the ST guides a user, for example, in determining a surgical corridor that is safe for the surrounding nerves.

In some embodiments, the time between updating ST may decline if the ST is low, typically indicating proximity to the nerve or lack of integrity of intervening tissue. In some embodiments, the algorithm may use uniform sized increments which vary with the stimulation frequency. In some embodiments, the algorithm may vary the increments logarithmically. In some embodiments, the algorithm may vary the increments according the ST.

Figure 3:
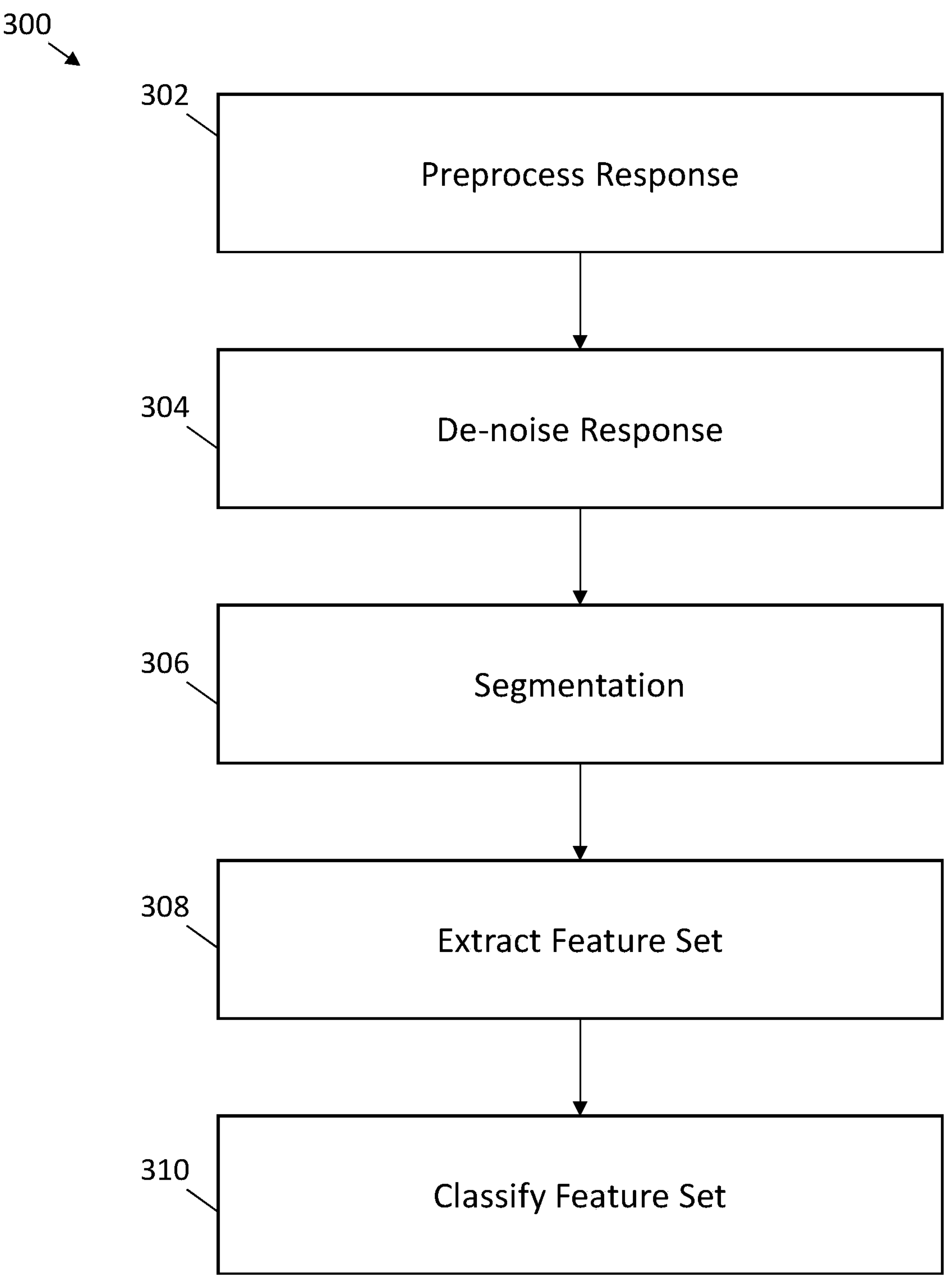
FIG. 3 shows an embodiment of a process for processing a response to stimulation and determining a stimulation threshold according to implementations of the current subject matter.

FIG. 3 illustrates an example embodiment of a method 300 for processing a response to stimulation and determining a stimulation threshold according to implementations of the current subject matter. The system can (e.g., automatically) cause stimulation of a nerve pathway of the patient with electrical pulses via electrodes placed over the nerve pathway coupled with or separate from a probe. The stimulation can generate a plurality of resultant electrical signals in the form of waveforms that can be recorded by the system, such as by a neuromonitoring device. The stimulation is applied to the patient at a set initial frequency, with increasing current levels (e.g., intensity) at a fixed current increment). In this approach, the stimulation is applied to the patient at a high frequency, and rising intensity level (e.g., see FIG. 2).

At 302, the response signal(s) can be preprocessed using one or more filtering techniques, mathematical transforms, or other preprocessing techniques. At 304, the response signal(s) can be denoised. Examples of the denoising process is described in U.S. patent application Ser. No. 15/927,921, filed Mar. 21, 2018, entitled "MEDICAL SYSTEMS AND METHODS FOR DETECTING CHANGES IN ELECTROPHYSIOLOGICAL EVOKED POTENTIALS," which is incorporated by reference herein in its entirety. For example, the system can include a processing circuit that can generate a plurality of evoked potential waveforms (EPs) based on the electrical potential data; calculate an ensemble average waveform (EA) of a subset of the plurality of EPs; apply a mathematical wavelet transform to the resultant EA; attenuate noise components from the transformed EA; and/or apply an inverse transform to the transformed EA to generate a denoised EA, among other things. In some implementations, the EA can be automatically denoised. In some implementations, the denoising method can include applying (e.g., automatically applying) at least one wavelet transform, such as a mathematical wavelet transform, to the EA. In some implementations, noise components can be attenuated from the transformed EA and/or an inverse transform can be applied to the transformed EA to generate a denoised EA.

At 306, the denoised response signals can be segmented. For example, one or more response signals can be grouped and/or otherwise collected.

At 308, one or more feature sets of the one or more groups of denoised response signals can be extracted. Each feature set may include one or more features of the collected signals and/or data. For example, a feature may include time complexity features, such as zero crossings, waveform length, minima and/or maxima counts, and/or the like. In some implementations, a feature may include a latency of the onset peak or a negative peak, the negative peak or peak to peak amplitude, a negative peak or rectified area (e.g., absolute value area) of the response, a duration and/or a rising or falling slope of the negative peak, and/or the like. In some implementations, the feature may include inter trough time (e.g. duration) of a CMAP, a CMAP amplitude, a spectral coherence, a linear prediction coefficient, an auto-regressive coefficient, and/or the like. The feature sets may be predetermined and/or automatically selected.

In some implementations, the feature can be included in a single feature set to classify a single epoch, or the feature can be included in a number N of feature sets, where N is the number of epochs being analyzed by the system. For example, in some implementations, if four epochs are analyzed, and only amplitude is considered, the system would extract four total features.

At 310, once the one or more feature sets are extracted, the system may classify the one or more feature sets, and/or one or more features of the feature sets using a classifier. Classification of the feature sets can help to determine a similarity between at least two response signals or groups of response signals. The classifier may include a statistical probability model (e.g., multi-variate Gaussian), a decision tree, support vector analysis, neural network, thresholding, a nearest neighbor, classifier, and/or the like. In some implementations, the classifier may include an auto-correlation between CMAPS and a time-series similarity metric between CMAPS (e.g., dynamic time warping). Thus, two or more response signals may be compared to confirm that a threshold has been reached.

Figure 4:
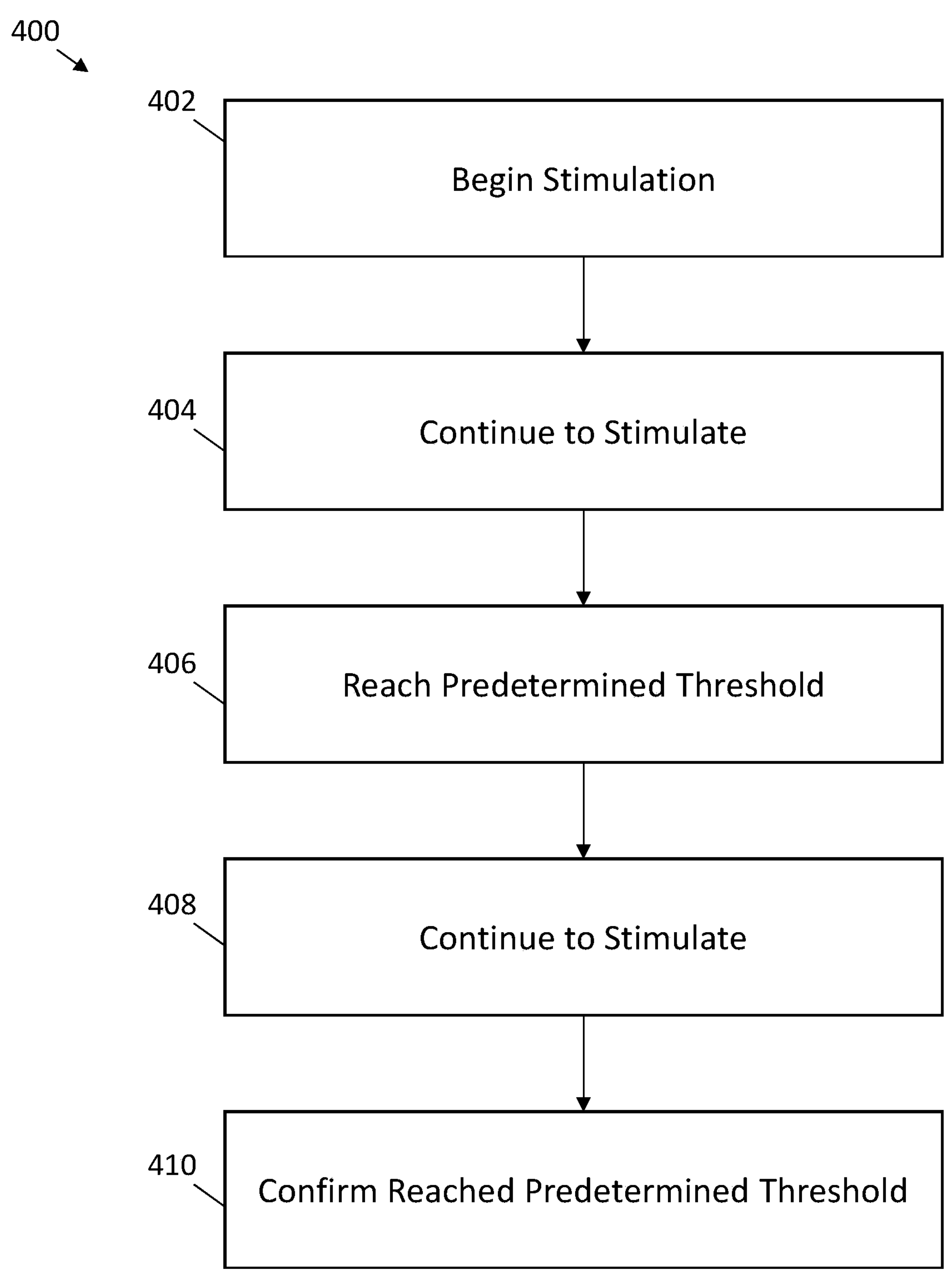
FIG. 4 shows an embodiment of a process for determining a stimulation threshold according to implementations of the current subject matter.

FIG. 4 illustrates an example embodiment of a method 400 for determining a lowest stimulation threshold current level using a neuromonitoring device according to implementations of the current subject matter. At 402, the system can (e.g., automatically) cause stimulation of a nerve pathway of the patient with electrical pulses via electrodes placed over the nerve pathway coupled with or separate from a probe. The stimulation pulses can be provided to the patient at an initial frequency and an initial current level. The stimulation can generate a plurality of resultant electrical signals in the form of waveforms that can be recorded by the system, such as by the neuromonitoring device.

At 404, the system can continue to cause stimulation of the nerve pathway of the patient by continuing to deliver stimulation pulses to the patient. The continued stimulation pulses can be delivered at the same or lower frequency. The continued stimulation pulses can be delivered with current levels (e.g., intensity) of one or more pulses at the same current level and/or that increase by a current increment or a variety of current increments. In this approach, the stimulation is applied to the patient at a high frequency, and rising intensity level (e.g., see FIG. 2).

At 406 the system can determine that a predetermined threshold is reached according to methods described herein based one or more response signal received by the system. Once the predetermined threshold is reached, the system continues to deliver stimulation pulses to the patient to evoke one or more additional muscular responses, at 408. After the predetermined threshold is reached, the system may continue to deliver stimulation pulses to the patient at a higher frequency, and increasing current levels. Continuing to deliver stimulation pulses after the threshold is reached can increase the quality of the response signals received by the system in response to the delivered stimulation pulses. The increased quality of the response signals can lead to more stable and/or repeatable responses, and threshold determinations.

At 410, the system can confirm or otherwise verify that the threshold is reached according to methods described herein. For example, the system can compare one or more response signals received by the system after the threshold is reached to each other, and/or to the initial response signal received when the threshold was reached, to determine whether the initial response signal is repeatable, as described herein. In some implementations, the system can extract one or more features from the collected response signals and classify the one or more features to determine whether the initial response signal is repeatable.

Figure 5:
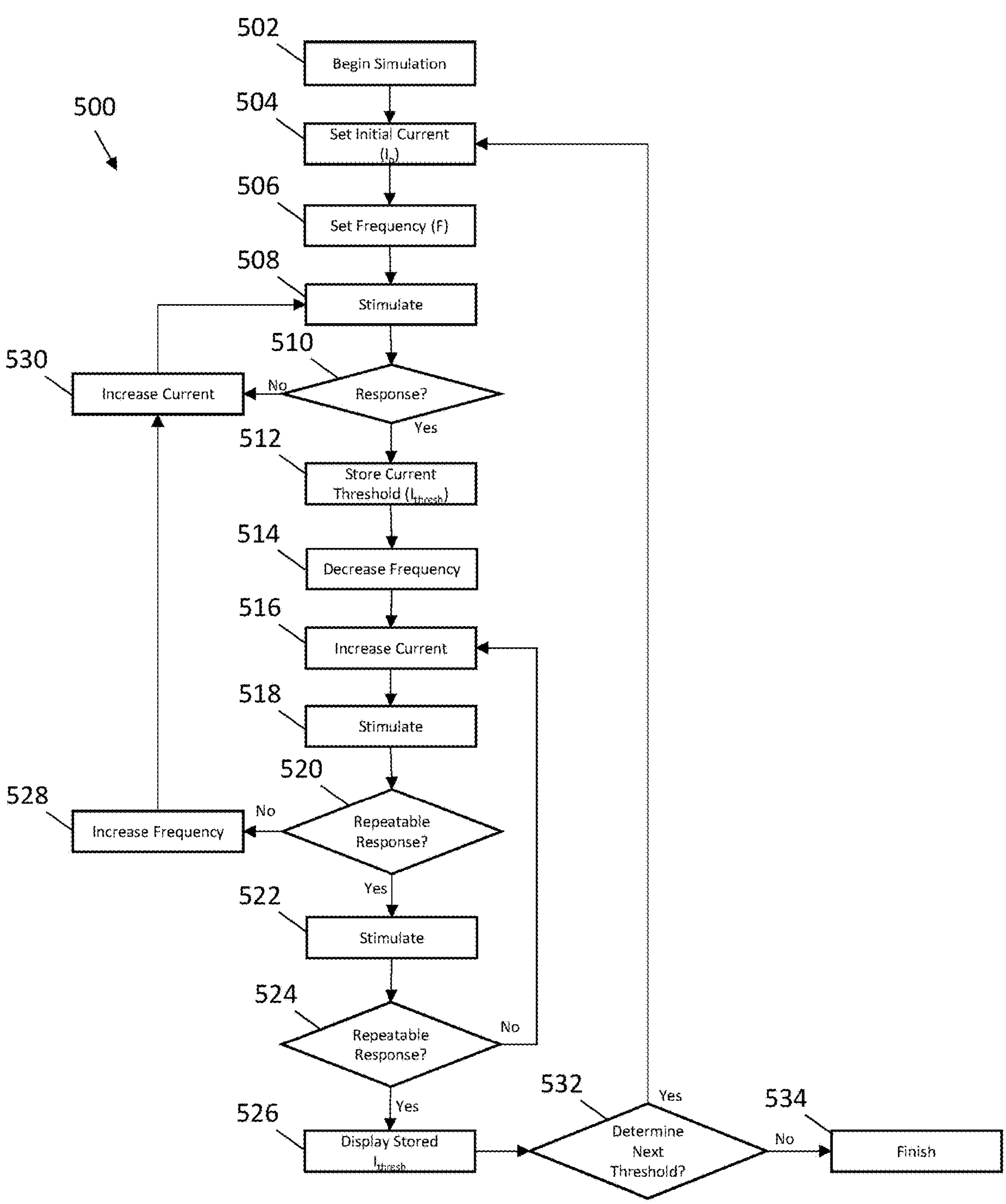
FIG. 5 shows an embodiment of a process for determining a stimulation threshold according to implementations of the current subject matter.

FIG. 5 illustrates an example embodiment of a method 500 for determining a lowest stimulation threshold current level using a neuromonitoring device according to implementations of the current subject matter. According to some embodiments, the method may automatically and/or quickly determine a stimulation current threshold after the device delivers one or more stimulation pulses to the patient. In an automated triggered electromyography or mechanomyography systems, it may be beneficial to determine the stimulation current threshold associated with a CMAP (e.g., a muscular response) that meets predetermined criteria. As mentioned above, in some EMG systems, a transient noise disturbance, spontaneous EMG spike or burst, and/or another anomaly may be improperly mistaken for an electrically elicited CMAP and lead to an erroneously identified threshold. For example, noise recorded by the device during a pulse sequence can result in false current threshold determinations. The systems described herein can help to reduce false-positives, and reduce or elimination noise disturbances.

Implementations of the device may confirm a current threshold, at least in part, by obtaining a repeatable muscle response resulting from continuing to stimulate the patient with one or more stimulation pulses after reaching the current threshold. As discussed below, the current threshold may be displayed via a display device.

At 502, stimulation of tissue associated with one or more muscles of a patient may begin. To stimulate the tissue of the patient, a stimulation probe may be used to provide one or more stimulation pulses, which act on one or more nearby nerves. In some embodiments, one or more electrodes attached to and/or separated from the stimulation probe may be used to provide the one or more stimulation pulses.

The patient's tissue may be stimulated, such as by the probe and/or electrodes, as a sequence of pulses. Generally, the stimulation pulses may be delivered by the device to the patient to approach the current threshold from below, by for example, incrementally increasing the stimulation current beginning at a lowest current level of a predetermined range of current levels. Methods described herein can improve the accuracy and/or repeatability of the displayed current threshold.

For example, the stimulation pulses can include a current level from within a predetermined range of current levels. At 504, the initial current level ($I_0$) may be set. The initial current level may be set to 0.5 mA or another low value. For example, the initial current level may be set to 0.25 mA, 0.75 mA, 1.0 mA, 1.25 mA, or more.

The initial current level may be predetermined as a low end point in the predetermined range of current values, and/or may be automatically selected based on certain conditions of the patient. The current level of one or more stimulation pulses in the sequence of pulses may be the same and/or increased from an immediately preceding pulse by a fixed current increment, such as by a first current increment. The first current increment can be set to 0.5 mA. In some embodiments, the first current increment is set to 0.25 mA, 0.75 mA, 1.0 mA, 1.25 mA, or more. The first current increment may be equal to the initial current level.

The stimulation pulses may be delivered at a predetermined frequency (e.g., a rate of stimulation). For example, at 506, the initial frequency may be set. The initial current level may be predetermined as a low end point in the predetermined range of current values, and/or may be automatically selected based on certain conditions of the patient. The initial frequency may be received by a user input device. The frequency may be initially set to 20 Hz, for example. In some embodiments, the frequency may be set to 5 Hz, 10 Hz, 15 Hz, 25 Hz, 30 Hz, or more.

At 508, the device may deliver one or more stimulation pulses to the patient. The current level of each stimulation pulse in the sequence of pulses may be automatically incremented by the current increment until a response that meets certain criteria is identified by the device. FIG. 2 illustrates an example of the sequence of pulses.

In some embodiments, the criteria may be predetermined. The criteria can include whether the muscular response reaches a predefined threshold. Other criteria, such as certain features, that may be included to determine whether incremental responses are repeatable and thus a predetermined threshold is reached could include the latency of the onset peak or a negative peak, the negative peak or peak to peak amplitude, a negative peak or rectified area (e.g., absolute value area) of the response, a duration and/or a rising or falling slope of the negative peak, and/or the like. In some implementations, the criteria, such as the feature, may include inter trough time (e.g. duration) of a CMAP, a CMAP amplitude, a spectral coherence, a linear prediction coefficient, an auto-regressive coefficient, and/or the like. The feature sets may be predetermined and/or automatically selected. In some implementations, the criteria includes time complexity features, such as zero crossings, waveform length, minima and/or maxima counts, and/or the like. In some implementations, a feature may include a latency of the onset.

Figure 6:
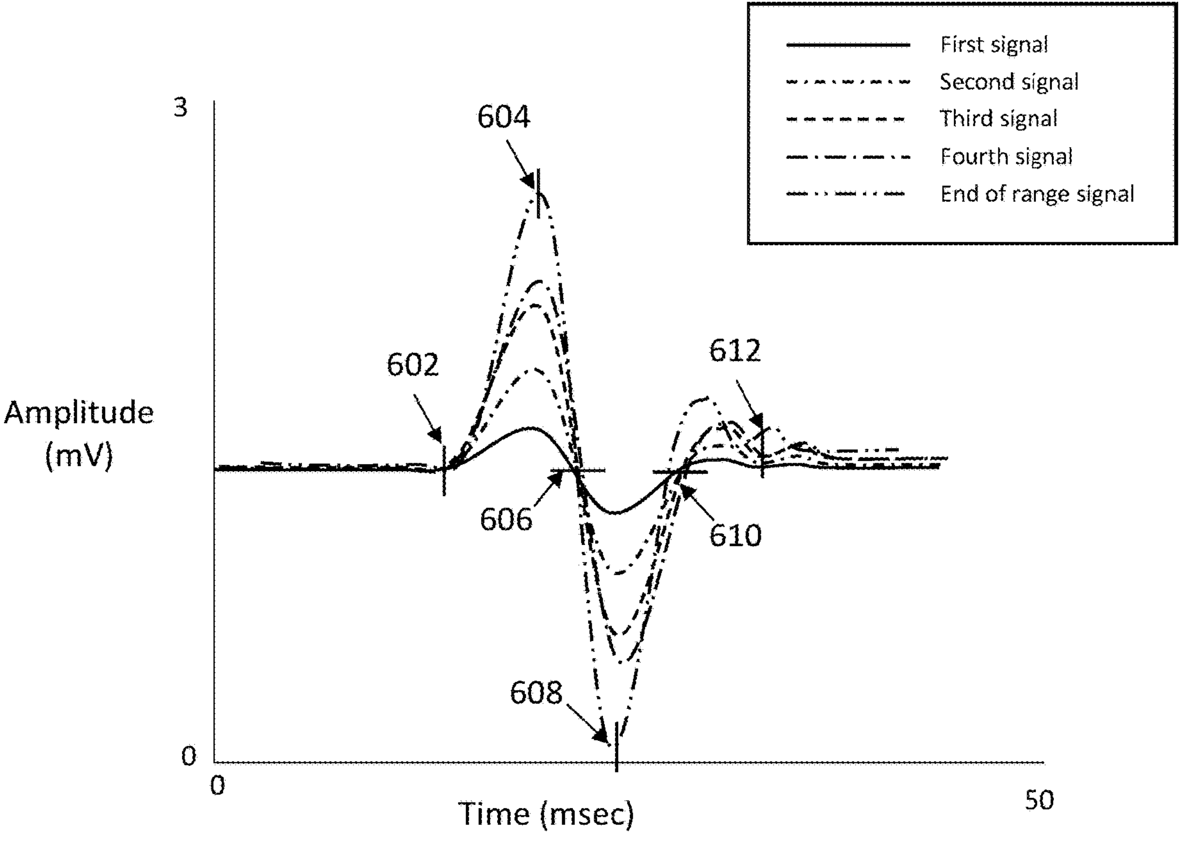
FIG. 6 shows an embodiment of an example epoch of waveform responses according to implementations of the current subject matter.

For example, FIG. 6 illustrates example response signals shown as waveforms received by the system in response to stimulation pulses being delivered to the patient. As shown in FIG. 6, the criteria for reaching a threshold can include the latency of the onset (e.g., a time at point 0 to the time at point 602) or a negative peak (e.g., the time at point 0 to the time at point 604), the negative peak (e.g., an amplitude at point 602 to point 604) or peak to peak (e.g., an amplitude at point 604 to point 608) amplitude, the negative peak (e.g., an area under the curve from point 602 to point 606) or rectified area of the response (e.g., a rectified area between point 602 to point 606 plus point 606 to point 610), a duration (e.g., the time from point 602 to point 612) and a rising (e.g., an amplitude and/or time from point 602 to point 604) or falling (e.g., an amplitude and/or time from point 604 to point 606) slope of the negative peak.

Figure 7:
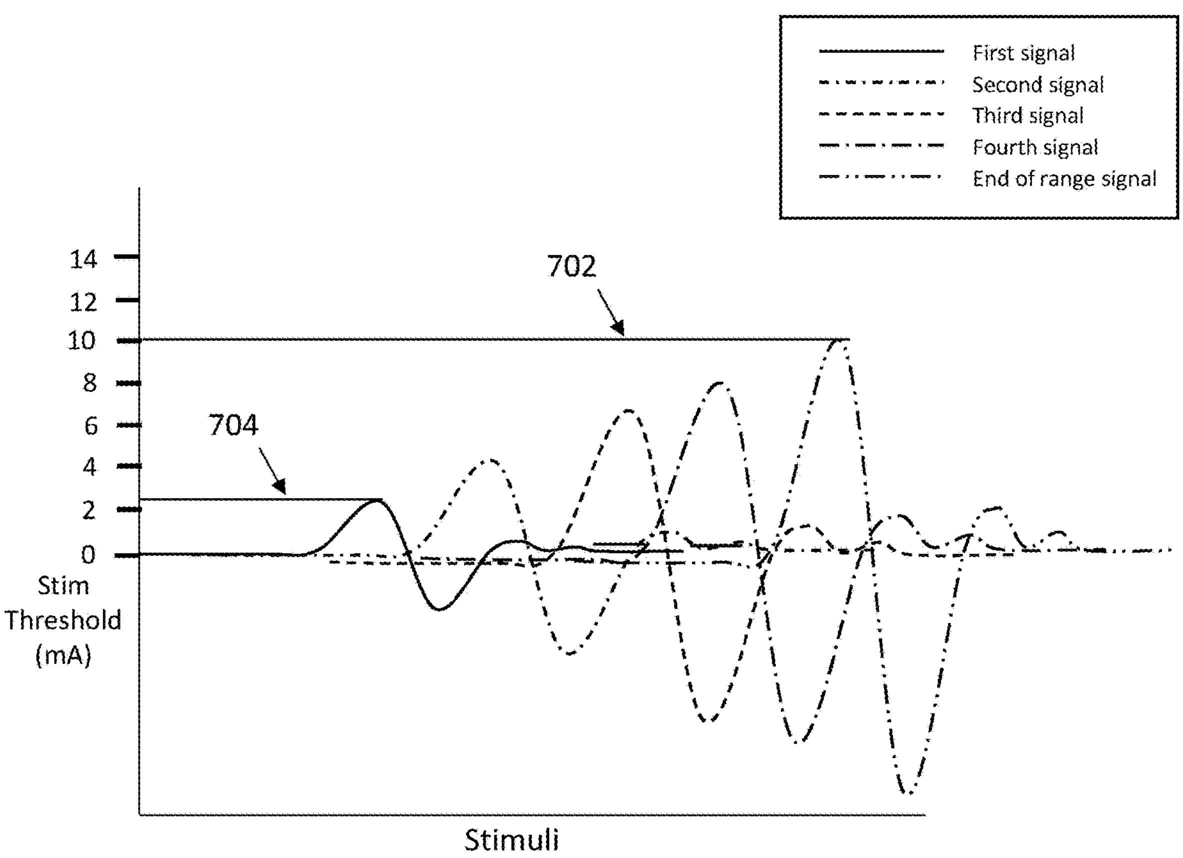
FIG. 7 shows an embodiment of an example epoch of waveform responses according to implementations of the current subject matter.

FIG. 7 illustrates other example response signals shown as waveforms received by the system in response to stimulation pulses being delivered to the patient. As shown in FIG. 7, the threshold current level may be predetermined, such as at current level 702 or current level 704.

Once the device receives and identifies a response that meets the criteria, the device may continue to deliver stimulation pulses, such as at a lower frequency and/or higher current level, which in some cases, have a current level that is high enough to evoke a muscular response.

For example, the sequence of stimulation pulses can include a first pulse and a second pulse delivered immediately after the first pulse. The first pulse can be delivered at a first current level from within the predetermined range of current levels and the second pulse can be delivered at a second current level from within the predetermined range of current levels. The second current level may be higher than the first current level. For example, the second current level can be higher than the first current level by an amount equal to the first current increment.

A first muscular or nerve response that meets the criteria (e.g., predetermined criteria) may be received in response to the tissue stimulation. For example, at 510 the system can determine whether a first response was received in response to a stimulation pulse that meets the criteria. In some implementations, the system may remove artifacts (e.g., noise) from the received signals, and/or may denoise the received signals according to implementations described herein. The system can receive a first response signal representing the muscular response. FIG. 4 illustrates example waveforms representing muscular responses received in response to one or more stimulation pulses delivered to the patient. If the system receives the response signal that meets the criteria, the system can, at 512, store the current level of the most recent pulse, and continue to deliver stimulation pulses to the patient. The stored current level can indicate a threshold current level ($I_{thresh}$)

If the system determines that the most recent pulse (e.g., a first evocation pulse) evoked a first muscular response that meets the criteria, the system may stimulate the tissue with at least one more stimulation pulse (e.g., a second evocation pulse) to evoke another muscular response (e.g., a second muscular response). When stimulating the patient's tissue with the second evocation pulse, the system can deliver one or more stimulation pulses in the sequence of pulses with the same or decreasing frequency of the delivery of each stimulation pulse (e.g., at 514) and/or at the same or increasing current level of one or more pulses in the sequence of pulses from the immediately preceding pulse by a second current increment (e.g., at 516). For example, the frequency can be decreased to 5 Hz (e.g., from 20 Hz). In some embodiments, the frequency is decreased to 2.5 Hz, 5 Hz, 7.5 Hz, 10 Hz, or more. The frequency of the delivery of stimulation pulses may be reduced to avoid muscular tetany. In some implementations, variable current increments may be implemented.

In some embodiments, the second current increment is equal to the first current increment (for example, the second current increment can be equal to 0.5 mA), or the current increments can be varied In some embodiments, the second current increment is larger than the first current increment.

In some embodiments, at 518, the system can deliver a number N additional stimulation pulses to the patient's tissue, where N=2, 3, 4, 5, 6, or more. The system may analyze the responses received in response to the N stimulation pulses sequentially and/or iteratively.

For example, the system may receive at least a second signal (and/or third signal, fourth signal, fifth signal, etc.) representing the second or more muscular response in response to the second or more evocation pulse delivered to the tissue. Thus, the system may determine that the second evocation pulse evokes the second muscular response.

At 520, the system can compare the first signal (see FIG. 4) received in response to the first evocation pulse and at least the second signal (see FIG. 4) received in response to the second evocation pulse. In some examples, the system can compare the signals sequentially. For example, the system can compare the first signal to the second signal, a third signal to the second signal, a fourth signal to the third signal, and/or a fifth signal to the fourth signal, etc. In some examples, the system can compare epochs of signals (e.g., pools of signals) simultaneously. For example, the system can compare the first signal, second signal, third signal, fourth signal, and/or fifth signal, among other signals at the same time.

At 520, if the system determines that at least two signals, such as the first and second signals, are repeatable, the system can display the stored threshold current level, at 526, on the user display. The signals may be determined as repeatable by comparing by one or more methods including onset or peak latency range, amplitude range, area, morphology, power, rectified area, power, upswing slope, downswing slope or segmented waveform characteristics. In some implementations, the system may classify one or more features extracted from the collected response signals to determine repeatability of the threshold response. The classifier may include a statistical probability model (e.g., multivariate Gaussian), a decision tree, support vector analysis, neural network, thresholding, a nearest neighbor, classifier, and/or the like. In some implementations, the classifier may include an auto-correlation between CMAPS and a time-series similarity metric between CMAPS (e.g., dynamic time warping). Thus, two or more response signals may be compared to confirm that a threshold has been reached. Additionally, at 520, the second, third, fourth and end of range response may vary significantly and may be differentiated from artifact by one or more of amplitude, morphology, area, slope, power or latency.

Figure 8A:
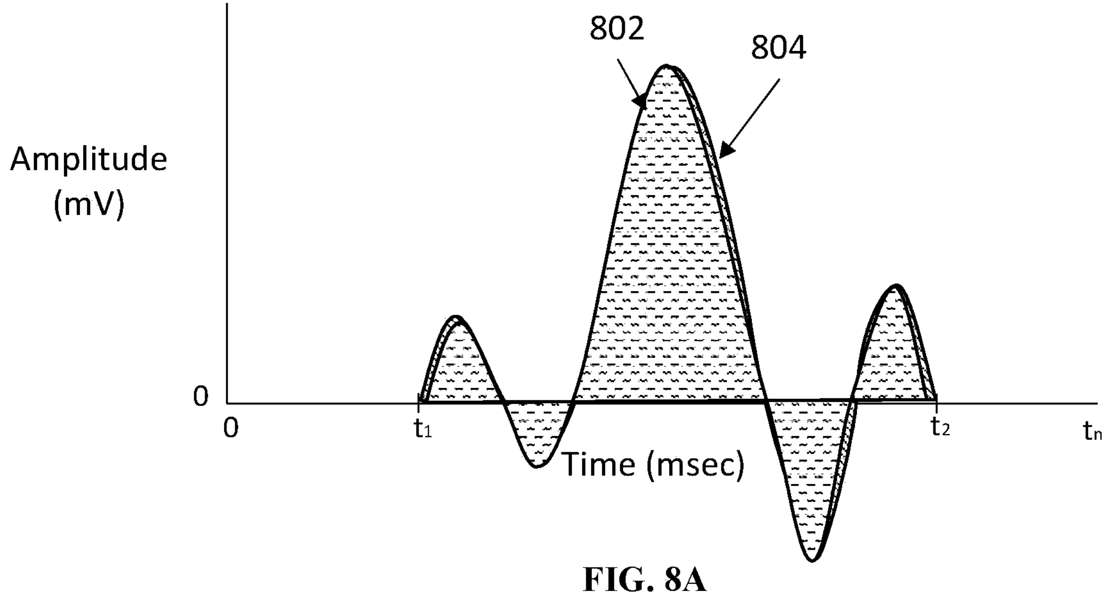
FIG. 8A shows an embodiment of example waveform responses according to implementations of the current subject matter.
Figure 8B:
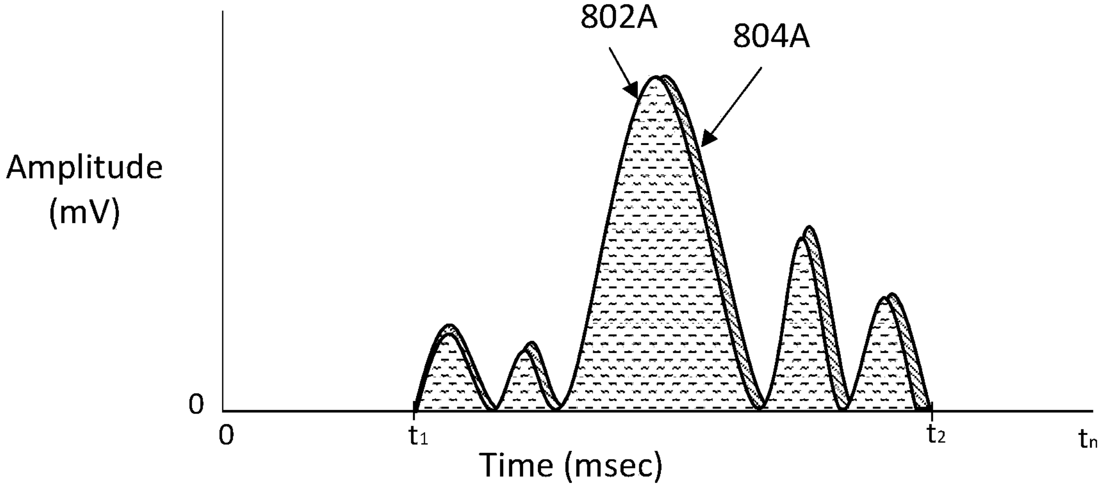
FIG. 8B shows an embodiment of example waveform responses according to implementations of the current subject matter.

FIGS. 8A and 8B illustrate example response signals received in response to the delivery of stimulation pulses to the patient. As shown in FIGS. 8A and 8B, a threshold response signal 802 and another subsequent response signal 804 can be compared for repeatability and confirmation that the threshold has been reached, such as using an area comparison method. Upon capturing one or more waveforms, the system can determine similarity between the waveforms over a time region of interest (e.g., from $t_1$ to $t_2$). A scaling factor k may be determined by dividing a peak to peak amplitude of the first waveform (e.g., waveform 802) shown in FIG. 8A by the peak to peak amplitude of the second waveform (e.g., waveform 804) shown in FIG. 8A. The waveforms may be converted to a rectified (absolute value) representation (see FIG. 8B). The area of the rectified first waveform 802A is calculated as $A_1$. The second rectified waveform 804A is multiplied by the scaling factor k to normalize the two amplitudes, and then subtracted from the first rectified waveform 802A in a point by point manner. The difference can then be integrated over the time region of interest to calculate a difference area, $A_{diff}$. Similarity, and thus repeatability, may be found when the difference area, $A_{diff}$, is less than a predetermined fraction (e.g. 20%) of the first waveform area, $A_1$.

At 522, in some embodiments, if the system determines that at least two signals are repeatable, such as the first and second signals, the system can again stimulate the patient's tissue with another evocation pulse having the same or higher current than a preceding evocation pulse. Here, the current level may or may not be incremented by the current increment. For example, the current level of the additional evocation pulse may be the same as the current level of the previous evocation pulse(s). At 524, the system can compare the additional signal(s), received in response to the additional evocation pulse(s), to at least the first two repeatable signals, such as the first and second signals, using methods described above. If the additional signal satisfies the criteria of similarity to the previously determined repeatable signals, the system may display the stored threshold current level on the user display, at 526.

In some embodiments, if at 520, the system determines that the analyzed signals, such as the first and second signals, are not repeatable, the system can increase the frequency of the pulses in the pulse sequence (e.g., to 20 Hz) at 528, and increase the current level at 530 by the current increment (e.g., by 0.5 mA). In some implementations, the frequency of the pulses may not change and/or may be lowered, and/or the current level may not change. The process may be repeated at 508 by delivering a sequence of stimulation pulses to the patient to determine whether additional evocation pulses are repeatable.

In some embodiments, if at 524 the system determines that the analyzed signals, such as the first, second signals, and/or additional signals are not repeatable or are caused by artifact, the system can increase the current level of the pulses in the pulse sequence by the current increment (e.g., by 0.5 mA), a t 516. The process may be repeated at 518 by continuing to deliver a sequence of stimulation pulses to the patient to determine whether additional evocation pulses are repeatable.

At 532, the system can determine whether delivery of stimulation pulses to the patient's tissue should continue, or determine whether to continue locating another current threshold by using the above noted criteria.

At 532, if the system determines that additional stimulation pulses should be delivered to the patient, the process may restart at 504. At 532, if the system determines that additional stimulation pulses should not be delivered to the patient, the process may finish at 534. In some embodiments, the process can be run in a single pass to yield a single current threshold result and finish, complete a stimulation sweep over an entire stimulation range, and/or be repeated to continuously display the value of a changing current threshold.

The systems, devices, apparatus, methods, algorithms, and other embodiments described herein can be utilized in connection with medical procedures, such as surgical procedures, and with medical and surgical instruments. For example, the various systems, devices, apparatus, methods, algorithms, and other embodiments can be utilized in medical procedures involving the spine or nervous system, or other types of procedures where it is desirable to monitor the health and/or integrity of nerves during the procedure. For example, the spinal surgery or other surgery can be performed by lateral approach or traditional anterior and/or posterior surgical approaches. Thus, the systems, devices, apparatus, methods, algorithms, and other embodiments can be integrated or used in connection with medical apparatus and instruments including, but not limited to, implants, rods, fixation devices, disc replacements, probes, dilators, retractors, pedicle screws, pedicle screw awls, nerve stimulators, curettes, forceps, needles, micro-dissectors, rongeurs, elevators, Jamshidi needles, rasps, gouges, surgical site lights or suction tubes.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing system, method and device descriptions and the diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, and algorithm steps described in connection with the examples disclosed herein may be implemented wholly or in part as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

Figure 9:
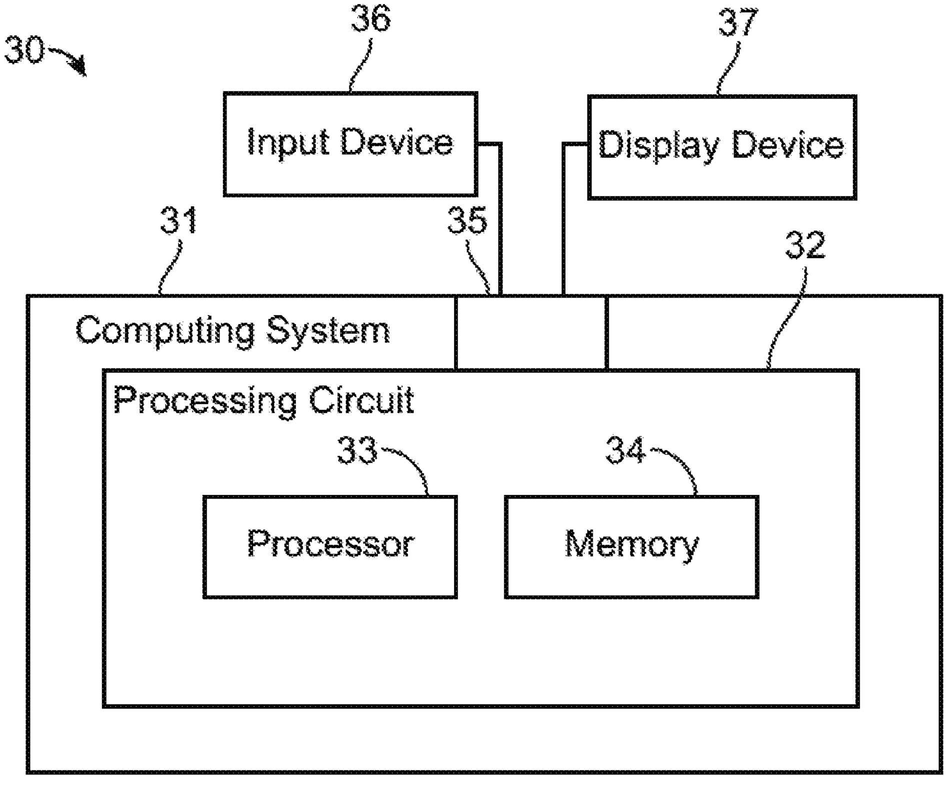
FIG. 9 is a block diagram of a model neuromonitoring device according to implementations of the current subject matter.

Referring to FIG. 9, according to some implementations of the current subject matter, the methods described above are implemented with neuromonitoring device 30. The device 30 includes hardware and software for operation and control of the system. According to some implementations, the device 30 includes a computing system 31, an input device 36, and a graphical alerting system, such as display device 37, among other components. The computing system comprises a processing circuit 32 having a processor 33 and memory 34. Processor 33 can be implemented as a general purpose processor, a digital signal processor (DSP), an application specific integrated circuit (ASIC), one or more field programmable gate arrays (FPGAs), a group of processing components, or other suitable electronic processing components or programmable logic device, discrete gate or transistor logic, discrete hardware components, or any combination thereof designed to perform the functions described herein. Memory 34 (e.g., memory, memory unit, storage device, etc.) is one or more devices (e.g., RAM, ROM, Flash-memory, hard disk storage, etc.) for storing data and/or computer code for completing or facilitating the various processes described in the present application. Memory 34 may be or include volatile memory or non-volatile memory. Memory 34 may include database components, object code components, script components, or any other type of information structure for supporting the various activities described in the present application. According to some implementations, memory 34 is communicably connected to processor 33 and includes computer code for executing one or more processes described herein. The memory 34 may contain a variety of modules, each capable of storing data and/or computer code related to specific types of functions.

Referring still to FIG. 9, the computing system 31 further includes a communication interface 35. The communication interface 35 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.).

Unless specifically stated otherwise, as apparent from the following discussions, it may be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A method for determining a stimulation threshold current level to avoid tetany associated with one or more muscles, the method comprising:

causing, by a stimulation system comprising one or more data processors, stimulation, via one or more electrodes, of tissue of a patient as a sequence of pulses delivered at a current level and a frequency, the causing including increasing the current level of each sequential pulse in the sequence of pulses by a first current increment;

determining, by the stimulation system, that a first evocation pulse from the sequence of pulses evokes a first muscular response, the first evocation pulse reaching predetermined criteria, the first evocation pulse having a first evocation current level, the first muscular response comprising a first evoked response that is processed by the stimulation system to classify the first evoked response;

causing, by the stimulation system, stimulation, via the one or more electrodes, of the tissue with a second evocation pulse from the sequence of pulses to evoke a second muscular response, the causing comprising:

maintaining or decreasing the frequency between each pulse in the sequence of pulses; and maintaining the current level of one or more pulses in the sequence of pulses at the current level of the first evocation pulse or increasing the current level of one or more pulses in the sequence of pulses from the immediately preceding pulse by a second current increment;

determining, by the stimulation system, that the second evocation pulse from the sequence of pulses evokes the second muscular response, the second muscular response comprising a second evoked response that is processed by the stimulation system to compare the first evoked response to the second evoked response; and storing, by the stimulation system, based at least in part on the determination that the first evocation pulse evokes the first muscular response and the determination that the second evocation pulse evokes the second muscular response, the first evocation current level as the stimulation threshold current level.

2. The method of claim 1, further comprising determining, by the stimulation system, that the first evocation pulse and the second evocation pulse are not due to artifact noise present within a first signal representing the first muscular response and artifact noise present within a second signal representing the second muscular response.

3. The method of claim 1, wherein the second current increment is equal to the first current increment.

4. The method of claim 1, wherein the determining that the first evocation pulse from the sequence of pulses evokes the first muscular response further comprises: storing the first evocation current level of the first evocation pulse.

5. The method of claim 1, wherein the determining that the first evocation pulse evokes the first muscular response includes receiving, by the stimulation system, a first signal representing the first muscular response and the determining that the second evocation pulse evokes the second muscular response includes receiving, by the stimulation system, a second signal representing the second muscular response.

6. The method of claim 5, further comprising:

comparing, by the stimulation system, the first signal to the second signal;

determining, by the stimulation system, that the first signal can be repeatably obtained-based on the comparison between the first signal and the second signal; and displaying, by the stimulation system, the first evocation current level of the first evocation pulse.

7. The method of claim 6, wherein the first signal and the second signal are compared as a group of signals that includes a third signal representing a third muscular response evoked in response to a third evocation pulse.

8. The method of claim 5, further comprising:

comparing, by the stimulation system, the first signal to the second signal;

determining, by the stimulation system, that the first signal is not repeatably obtained based on the comparison between the first signal and the second signal;

causing, by the stimulation system, stimulation of the tissue with a third evocation pulse from the sequence of pulses to evoke a third muscular response, the causing comprising:

increasing or maintaining, by the stimulation system, the frequency between each pulse in the sequence of pulses; and increasing, by the stimulation system, the current level of each pulse in the sequence of pulses from the immediately preceding pulse or maintaining the current level of each pulse in the sequence of pulses from the immediately preceding pulse.

9. The method of claim 1, wherein the processing of the first evoked response comprises preprocessing the first evoked response using one or more filtering techniques or mathematical transforms.

10. The method of claim 1, wherein the processing of the second evoked response comprises preprocessing the first evoked response using one or more filtering techniques or mathematical transforms.

11. A method for determining a stimulation threshold current level in a group of channels of a neuromonitoring device, wherein each channel of the group of channels is associated with one or more muscles, the method comprising:

causing, by a stimulation system comprising one or more data processors, stimulation, via one or more electrodes, of tissue within a predetermined range of current levels as a sequence of pulses delivered at a frequency by delivering stimulation signals, the sequence of pulses including:

a first pulse delivered at a first current level within the predetermined range of current levels; and a second pulse delivered at a second current level within the predetermined range of current levels, the first pulse being delivered immediately preceding the second pulse, and the second current level being higher than the first current level;

determining that the second pulse evokes a first muscular response, the first muscular response comprising a first evoked response that is processed by the stimulation system to classify the first evoked response;

causing, by the stimulation system, stimulation, via the one or more electrodes, the tissue with a third pulse from the sequence of pulses to evoke a second muscular response, the third pulse being delivered at a third current level that is equal to or higher than the second current level;

determining that the third pulse evokes the second muscular response; and storing, by the stimulation system, based at least in part on the determination that the second pulse evokes the first muscular response and the determination that the third pulse evokes the second muscular response, the second current level as the stimulation threshold current level.

12. The method of claim 11, further comprising determining, by the stimulation system, that the first pulse and the second pulse are not due to artifact noise present within a first signal representing the first muscular response and artifact noise present within a second signal representing the second muscular response.

13. The method of claim 11, wherein the stimulating further comprises:

decreasing or maintaining, by the stimulation system, the frequency between each pulse in the sequence of pulses; and increasing, by the stimulation system, the current level of the third pulse by an amount that is greater than a difference between the first current level and the second current level.

14. The method of claim 11, wherein the determining that the second pulse evokes the first muscular response includes receiving, by the stimulation system, a first signal representing the first muscular response and the determining that the third pulse evokes the second muscular response includes receiving by the stimulation system, a second signal representing the second muscular response.

15. The method of claim 14, further comprising:

comparing, by the stimulation system, the first signal with the second signal;

determining, by the stimulation system, that the first signal can be repeatably obtained-based on the comparison between the first signal and the second signal; and displaying, by the stimulation system, the second current level of the second pulse.

16. The method of claim 15, wherein the first signal and the second signal are compared as a group of signals that includes a third signal representing a third muscular response evoked in response to a third evocation pulse.

17. The method of claim 15, further comprising:

comparing, by the stimulation system, the first signal with the second signal;

determining, by the stimulation system, that the first signal is not repeatably obtained based on the comparison between the first signal and the second signal;

causing, by the stimulation system, stimulation of the tissue with a fourth pulse from the sequence of pulses to evoke a third muscular response, the causing comprising:

increasing or maintaining, by the stimulation system, the frequency between each pulse in the sequence of pulses; and increasing, by the stimulation system, the current level of each pulse in the sequence of pulses from the immediately preceding pulse or maintaining the current level of each pulse in the sequence of pulses from the immediately preceding pulse.

18. A stimulation system for detecting and identifying a stimulation threshold to avoid tetany of a patient's muscles, wherein the system comprises:

at least one processor; and at least one memory storing instructions which, when executed by the at least one processor, result in operations comprising:

causing, by the stimulation system, stimulation, via one or more electrodes, of the patient's tissue with a sequence of pulses delivered at a current level and a frequency, the causing including increasing the current level of each sequential pulse in the sequence of pulses;

determining, by the stimulation system, that a first evocation pulse from the sequence of pulses evokes a first muscular response, the first evocation pulse having a first evocation current level;

continuing to cause, by the stimulation system, stimulation of the patient's tissue with a second evocation pulse from the sequence of pulses to evoke a second muscular response, the causing comprising:

maintaining or decreasing the frequency between each pulse in the sequence of pulses; and maintaining or increasing the current level of each pulse in the sequence of pulses from the immediately preceding pulse by a second current increment;

determining, by the stimulation system, that the second evocation pulse from the sequence of pulses evokes the second muscular response; and storing, by the stimulation system, based at least in part on the determination that the first evocation pulse evokes the first muscular response and the determination that the second evocation pulse evokes the second muscular response, the first evocation current level as the stimulation threshold current level.

19. The system of claim 18, wherein the operations further comprise determining, by the stimulation system, that the first evocation pulse and the second evocation pulse are not due to artifact noise present within a first signal representing the first muscular response and artifact noise present within a second signal representing the second muscular response.

* * * * *